(12) United States Patent
Greenberg et al.

(10) Patent No.: US 10,201,697 B2
(45) Date of Patent: *Feb. 12, 2019

(54) FLEXIBLE CIRCUIT ELECTRODE ARRAY WITH WIRE OR FILM SUPPORT

(71) Applicant: Second Sight Medical Products, Inc., Sylmar, CA (US)

(72) Inventors: Robert J Greenberg, Los Angeles, CA (US); Eugene de Juan, San Francisco, CA (US); Mark S Humayun, Glendale, CA (US); Kelly McClure, Simi Valley, CA (US); Neil Hamilton Talbot, La Crescenta, CA (US); Jordan Matthew Neysmith, Mountain View, CA (US); Brian V Mech, Santa Clarita, CA (US); James Singleton Little, Arvada, CO (US); Mohamed Khaldi, Los Angeles, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/823,459

(22) Filed: Nov. 27, 2017

(65) Prior Publication Data

US 2018/0178002 A1    Jun. 28, 2018

Related U.S. Application Data

(62) Division of application No. 12/032,627, filed on Feb. 15, 2008, now Pat. No. 9,861,809.
(Continued)

(51) Int. Cl.
*A61N 1/00* (2006.01)
*A61N 1/05* (2006.01)
(Continued)

(52) U.S. Cl.
CPC ......... *A61N 1/0543* (2013.01); *A61N 1/0541* (2013.01); *A61N 1/05* (2013.01); *H05K 1/0393* (2013.01); *H05K 1/118* (2013.01)

(58) Field of Classification Search
CPC ...... A61N 1/05; A61N 1/0541; A61N 1/0543; H05K 1/0393; H05K 1/118
See application file for complete search history.

(56) References Cited

U.S. PATENT DOCUMENTS 4,573,481 A  12/1986  Bullara
4,628,933 A  12/1986  Michelson
(Continued)

*Primary Examiner* — Mallika D Fairchild
(74) *Attorney, Agent, or Firm* — Scott Dunbar

(57) ABSTRACT

The disclosure relates to a flexible circuit electrode array comprising: a polymer base layer; metal traces deposited on said polymer base layer, including electrodes suitable to stimulate neural tissue; a polymer top layer deposited on said polymer base layer and said metal traces; and at least one support embedded in said array. The disclosure further relates to a flexible circuit electrode array comprising: a polymer base layer; metal traces deposited on said polymer base layer, including electrodes suitable to stimulate neural tissue; a polymer top layer deposited on said polymer base layer and said metal traces; and a folded flexible circuit cable connecting the electrode array with an interconnection pad. The disclosure further relates to a method of making a flexible circuit electrode array comprising: depositing a polymer base layer; depositing metal on said polymer base layer; patterning said metal to form metal traces; depositing a polymer top layer on said polymer base layer and said metal traces; heating said flexible circuit electrode array in a mold to form a three dimensional shape in said flexible circuit electrode array, embedding a support at least in the base layer, top layer or between the base and top layer,
(Continued)

and/or folding a flexible circuit cable at least once connecting the electrode array with an interconnection pad on the array.

15 Claims, 33 Drawing Sheets

Related U.S. Application Data

(60) Provisional application No. 60/901,907, filed on Feb. 16, 2007.

(51) Int. Cl.
*H05K 1/03* (2006.01)
*H05K 1/11* (2006.01)

(56) References Cited

U.S. PATENT DOCUMENTS

| | | | |
|---|---|---|---|
| 4,837,049 A | | 6/1989 | Byers et al. |
| 5,109,844 A | | 5/1992 | de Juan, Jr. et al. |
| 5,215,088 A | | 6/1993 | Normann et al. |
| 5,919,220 A | * | 7/1999 | Stieglitz .............. A61N 1/0556 600/377 |
| 5,935,155 A | | 8/1999 | Humayun et al. |
| 6,400,989 B1 | | 6/2002 | Eckmiller |
| 6,458,157 B1 | | 10/2002 | Suaning |
| 2003/0097165 A1 | * | 5/2003 | Krulevitch .......... A61N 1/0543 607/115 |

* cited by examiner

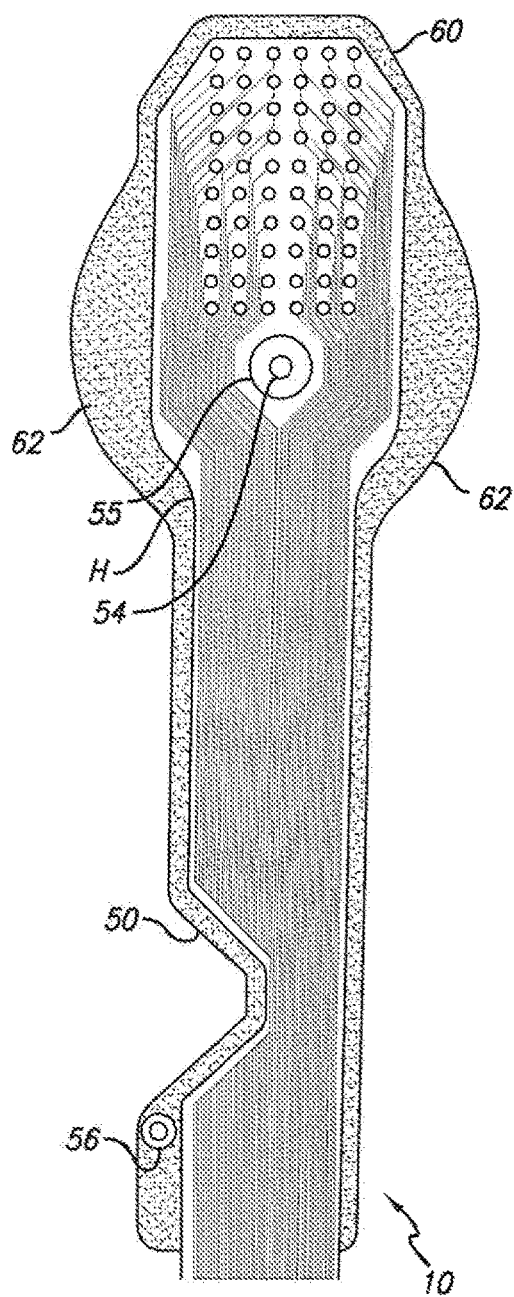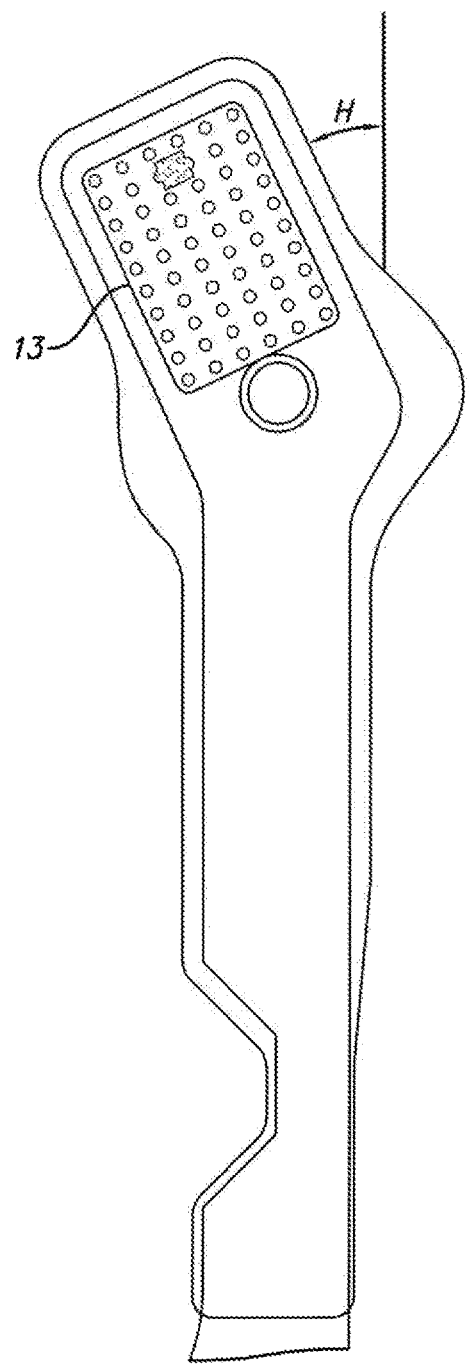

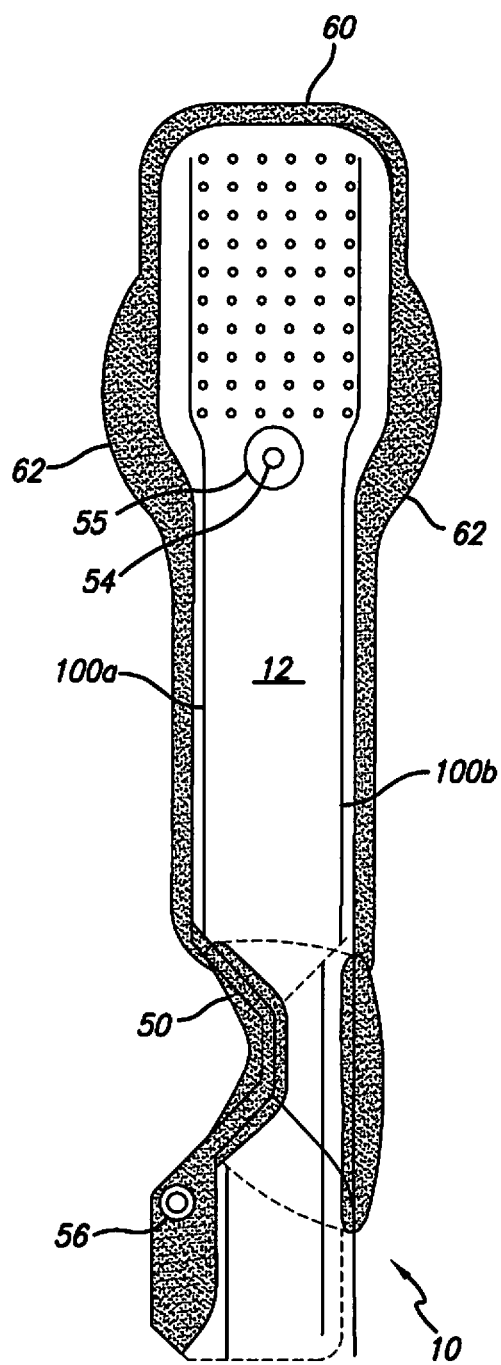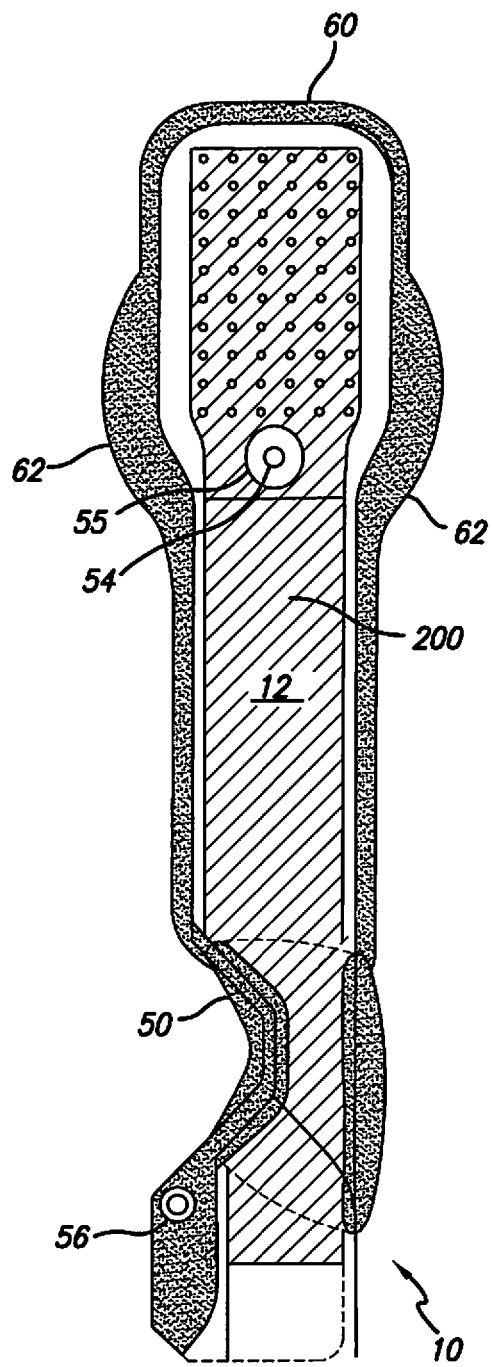
FIG. 20C
FIG. 20D

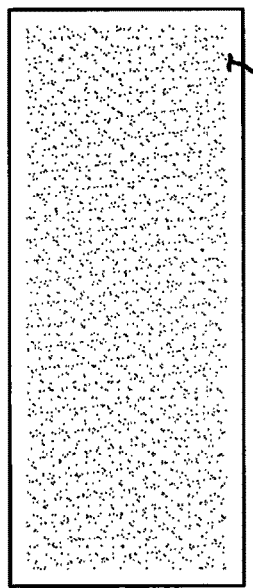
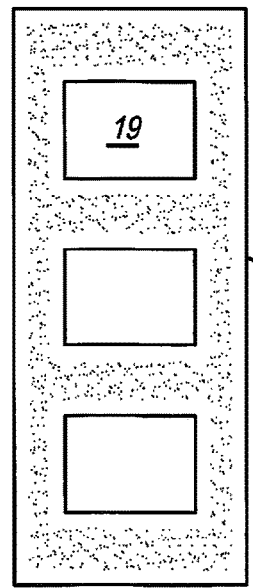
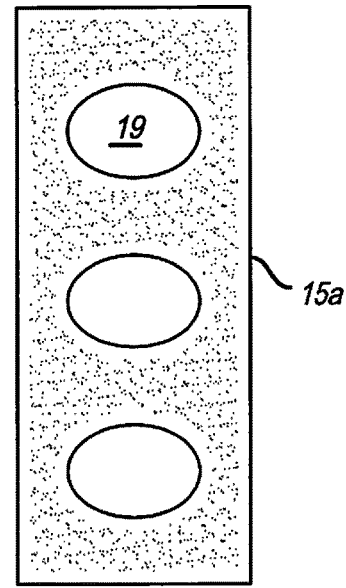
FIG. 31　　FIG. 32　　FIG. 33
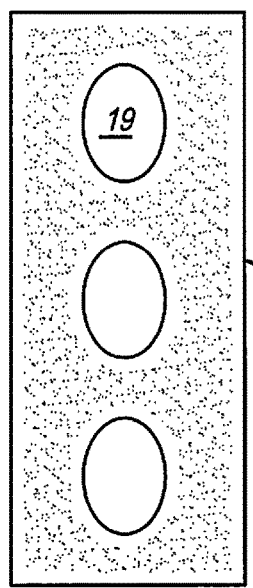
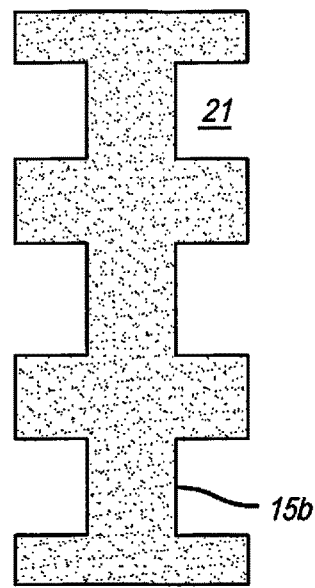
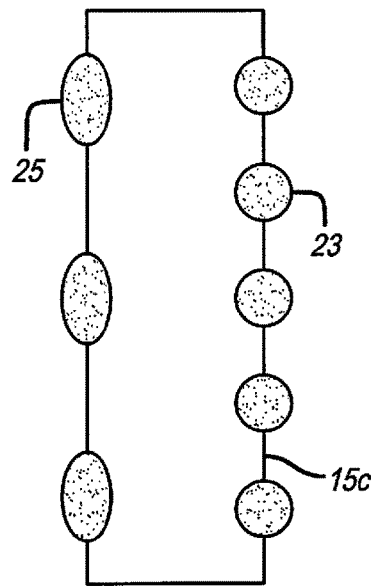
FIG. 34　　FIG. 35　　FIG. 36

FLEXIBLE CIRCUIT ELECTRODE ARRAY WITH WIRE OR FILM SUPPORT

CROSS-REFERENCE TO RELATED APPLICATIONS

This application is a divisional application of U.S. patent application Ser. No. 12/032,627, filed Feb. 15, 2008, for Flexible Circuit Electrode Array with Wire or Film Support, which claims the benefit of U.S. Provisional Application No. 60/901,907, Flexible Circuit Electrode Array with Wire or Film Support, filed Feb. 16, 2007 and this application claims the benefit of U.S. Provisional Application No. 60/901,947, Flexible Circuit Electrode Array with a Folded Flexible Array Cable, filed Feb. 16, 2007, the disclosures of both are incorporated herein by reference.

GOVERNMENT RIGHTS NOTICE

This invention was made with government support under grant No. R24EY12893-01, awarded by the National Institutes of Health. The government has certain rights in the invention.

FIELD OF THE INVENTION

The present invention is generally directed to neural stimulation and more specifically to an improved electrode array for neural stimulation with a support including at least one wire or film or foil embedded in the array and to flexible circuit electrode array with a folded flexible array cable.

BACKGROUND OF THE INVENTION

In 1755 LeRoy passed the discharge of a Leyden jar through the orbit of a man who was blind from cataract and the patient saw "flames passing rapidly downwards." Ever since, there has been a fascination with electrically elicited visual perception. The general concept of electrical stimulation of retinal cells to produce these flashes of light or phosphenes has been known for quite some time. Based on these general principles, some early attempts at devising prostheses for aiding the visually impaired have included attaching electrodes to the head or eyelids of patients. While some of these early attempts met with some limited success, these early prosthetic devices were large, bulky and could not produce adequate simulated vision to truly aid the visually impaired.

In the early 1930's, Foerster investigated the effect of electrically stimulating the exposed occipital pole of one cerebral hemisphere. He found that, when a point at the extreme occipital pole was stimulated, the patient perceived a small spot of light directly in front and motionless (a phosphene). Subsequently, Brindley and Lewin (1968) thoroughly studied electrical stimulation of the human occipital (visual) cortex. By varying the stimulation parameters, these investigators described in detail the location of the phosphenes produced relative to the specific region of the occipital cortex stimulated. These experiments demonstrated: (1) the consistent shape and position of phosphenes; (2) that increased stimulation pulse duration made phosphenes brighter; and (3) that there was no detectable interaction between neighboring electrodes which were as close as 2.4 mm apart.

As intraocular surgical techniques have advanced, it has become possible to apply stimulation on small groups and even on individual retinal cells to generate focused phosphenes through devices implanted within the eye itself. This has sparked renewed interest in developing methods and apparati to aid the visually impaired. Specifically, great effort has been expended in the area of intraocular retinal prosthesis devices in an effort to restore vision in cases where blindness is caused by photoreceptor degenerative retinal diseases; such as retinitis pigmentosa and age related macular degeneration, which affect millions of people worldwide.

Neural tissue can be artificially stimulated and activated by prosthetic devices that pass pulses of electrical current through electrodes on such a device. The passage of current causes changes in electrical potentials across visual neuronal membranes, which can initiate visual neuron action potentials, which are the means of information transfer in the nervous system.

Based on this mechanism, it is possible to input information into the nervous system by coding the sensory information as a sequence of electrical pulses which are relayed to the nervous system via the prosthetic device. In this way, it is possible to provide artificial sensations including vision. One typical application of neural tissue stimulation is in the rehabilitation of the blind. Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretinal). This placement must be mechanically stable, minimize the distance between the device electrodes and the visual neurons, control the electronic field distribution and avoid undue compression of the visual neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 µA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. Each spike pierces cortical tissue for better electrical contact.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., E. de Juan, et al., 99 Am. J. Ophthalmol. 272 (1985). These retinal tacks have proved to be biocompatible and remain embedded in the retina and choroid/sclera, effectively pinning the retina against the choroid and the posterior aspects of the globe. Retinal tacks are one way to attach a retinal electrode array to the retina. U.S. Pat. No. 5,109,844 to de Juan describes a flat electrode array placed against the retina for visual stimulation. U.S. Pat. No. 5,935,155 to Humayun describes a retinal prosthesis for use with the flat retinal array described in de Juan.

SUMMARY OF THE INVENTION

Polymer materials are useful as electrode array bodies for neural stimulation. They are particularly useful for retinal stimulation to create artificial vision, cochlear stimulation to create artificial hearing, or cortical stimulation for many purposes. Regardless of which polymer is used, the basic construction method is the same. A layer of polymer is laid down, commonly by some form of chemical vapor deposition, spinning, meniscus coating, or casting. A layer of metal, preferably platinum, is applied to the polymer and patterned to create electrodes and leads for those electrodes. Patterning is commonly done by photolithographic methods. A second layer of polymer is applied over the metal layer and patterned to leave openings for the electrodes, or openings are created later by means such as laser ablation. Hence the array and its supply cable are formed of a single body. Alternatively, multiple alternating layers of metal and polymer may be applied to obtain more metal traces within a given width.

The pressure applied against the retina, or other neural tissue, by an electrode array is critical. Too little pressure causes increased electrical resistance between the array and retina, along with electric field dispersion. Too much pressure may block blood flow causing retinal ischemia and hemorrhage. Pressure on the neural retina may also block axonal flow or cause neuronal atrophy leading to optic atrophy. Common flexible circuit fabrication techniques such as photolithography generally require that a flexible circuit electrode array be made flat. Since the retina is spherical, a flat array will necessarily apply more pressure near its edges, than at its center. Further, the edges of a flexible circuit polymer array may be quite sharp and cut the delicate retinal tissue. With most polymers, it is possible to curve them when heated in a mold. By applying the right amount of heat to a completed array, a curve can be induced that matches the curve of the retina. With a thermoplastic polymer such as liquid crystal polymer, it may be further advantageous to repeatedly heat the flexible circuit in multiple molds, each with a decreasing radius. Further, it is advantageous to add material along the edges of a flexible circuit array to make the edges less sharp and/or more compliant. Particularly, it is advantageous to add material that is more compliant than the polymer used for the flexible circuit array so that the edges of the array conform more readily to the retina and are therefore less likely to cause damage to the retina.

It is further advantageous to provide a fold or twist in the flexible circuit array at the point where it passes through the sclera in order to reduce the size of the array cable in the trans-scleral region to minimize the possibility of leakage at the sclerotomy. Another reason for folding or twisting the array cable at the sclerotomy is to flip the array head so the electrodes are facing the retina. Additional material may be added inside and outside the fold to promote a good seal with the scleral tissue.

The novel features of the invention are set forth with particularity in the appended claims. The invention will be best understood from the following description when read in conjunction with the accompanying drawings.

One aspect of the invention is a flexible circuit electrode array comprising: a polymer base layer; metal traces deposited on said polymer base layer, including electrodes suitable to stimulate neural tissue; a polymer top layer deposited on said polymer base layer and said metal traces; and at least one support embedded in said array.

Another aspect of the invention is a flexible circuit electrode array comprising: a polymer base layer; metal traces deposited on said polymer base layer, including electrodes suitable to stimulate neural tissue; a polymer top layer deposited on said polymer base layer and said metal traces; and a folded flexible circuit cable connecting the electrode array with an interconnection pad.

Another aspect of the invention is a method of making a flexible circuit electrode array comprising: depositing a polymer base layer; depositing metal on said polymer base layer; patterning said metal to form metal traces; depositing a polymer top layer on said polymer base layer and said metal traces; heating said flexible circuit electrode array in a mold to form a three dimensional shape in said flexible circuit electrode array; embedding a support at least in the base layer, top layer or between the base and top layer; and/or folding a flexible circuit cable at least once connecting the electrode array with an interconnection pad on the array.

Another aspect of the invention is a method of applying an additional layer or two layers of softer polymer, such as silicone, over said flexible circuit to provide a softer interface to the retina. A support may be embedded in said softer polymer layer(s) to provide greater shape control and pressure uniformity on the retina.

BRIEF DESCRIPTION OF THE DRAWINGS

FIG. 19A depicts another variation without the horizontal angle between the flexible electrode array and the flexible cable.

FIG. 19B depicts a top view of a flexible circuit array and flexible circuit cable showing an additional horizontal angle between the flexible electrode array and the flexible cable.

FIG. 20C depicts another variation without the horizontal angle between the flexible electrode array and the flexible cable but with an orientation of the electrodes in the flexible electrode array as shown for the variation in FIG. 19A with two wires.

FIG. 20D depicts another variation without the horizontal angle between the flexible electrode array and the flexible cable but with an orientation of the electrodes in the flexible electrode array as shown for the variation in FIG. 19A with a film or foil.

FIG. 31 depicts a soft polymer flange applied to an array cable.

FIG. 32 depicts a soft polymer ladder with a rectangular cut out applied to an array cable.

FIG. 33 depicts a soft polymer ladder with horizontal cutouts applied to an array cable.

FIG. 34 depicts a soft polymer ladder with vertical cutouts applied to an array cable.

FIG. 35 depicts a soft polymer skeleton structure applied to an array cable.

FIG. 36 depicts a soft polymer beads and bumpers applied to an array cable.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

The present invention is generally directed to neural stimulation and more specifically to an improved electrode array for neural stimulation with a support including at least one wire or film or foil embedded in the array.

Figure 1:
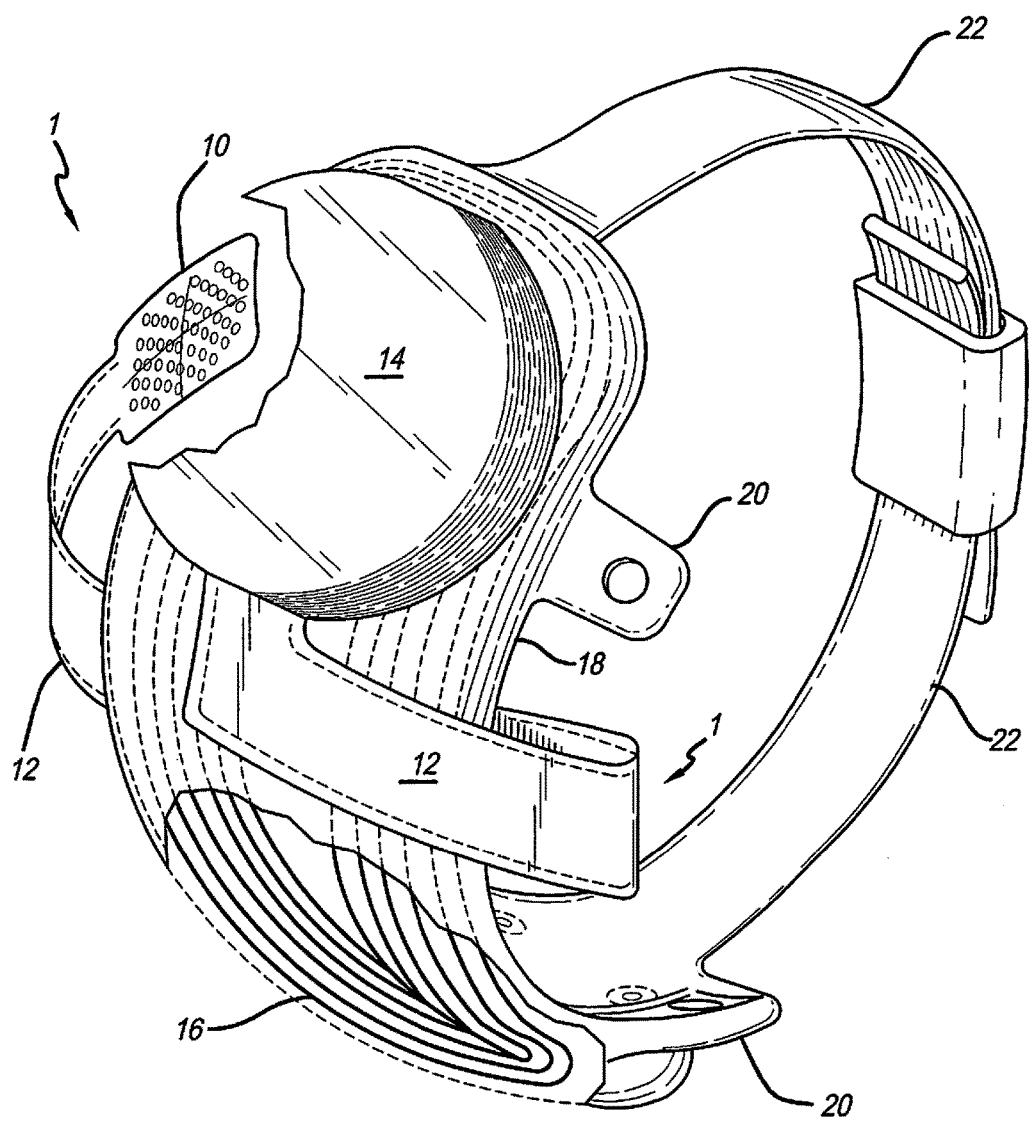
FIG. 1 is a perspective view of the implanted portion of the preferred retinal prosthesis.

FIG. 1 shows a perspective view of the implanted portion of the preferred retinal prosthesis. A flexible circuit 1 includes a flexible circuit electrode array 10 which is mounted by a retinal tack (not shown) or similar means to the epiretinal surface. The flexible circuit electrode array 10 is electrically coupled by a flexible circuit cable 12, which pierces the sclera and is electrically coupled to an electronics package 14, external to the sclera.

The electronics package 14 is electrically coupled to a secondary inductive coil 16. Preferably the secondary inductive coil 16 is made from wound wire. Alternatively, the secondary inductive coil 16 may be made from a flexible circuit polymer sandwich with wire traces deposited between layers of flexible circuit polymer. The electronics package 14 and secondary inductive coil 16 are held together by a molded body 18. The molded body 18 may also include suture tabs 20. The molded body 18 narrows to form a strap 22 which surrounds the sclera and holds the molded body 18, secondary inductive coil 16, and electronics package 14 in place. The molded body 18, suture tabs 20 and strap 22 are preferably an integrated unit made of silicone elastomer. Silicone elastomer can be formed in a pre-curved shape to match the curvature of a typical sclera. However, silicone remains flexible enough to accommodate implantation and to adapt to variations in the curvature of an individual sclera. The secondary inductive coil 16 and molded body 18 are preferably oval shaped. A strap 22 can better support an oval shaped coil.

It should be noted that the entire implant is attached to and supported by the sclera. An eye moves constantly. The eye moves to scan a scene and also has a jitter motion to improve acuity. Even though such motion is useless in the blind, it often continues long after a person has lost their sight. By placing the device under the rectus muscles with the electronics package in an area of fatty tissue between the rectus muscles, eye motion does not cause any flexing which might fatigue, and eventually damage, the device.

Figure 2:
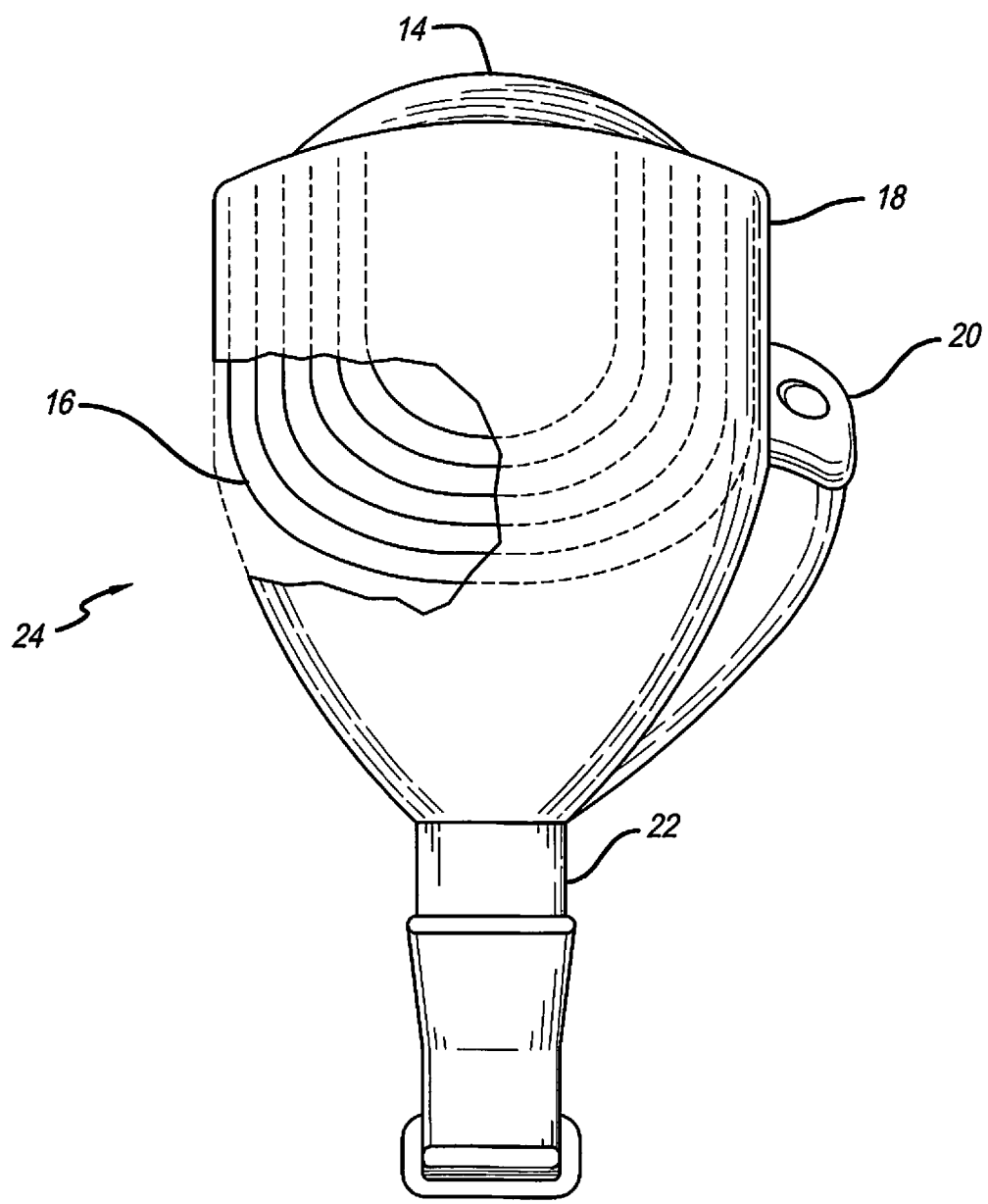
FIG. 2 is a side view of the implanted portion of the preferred retinal prosthesis showing the fan tail in more detail.
Figure 3A:
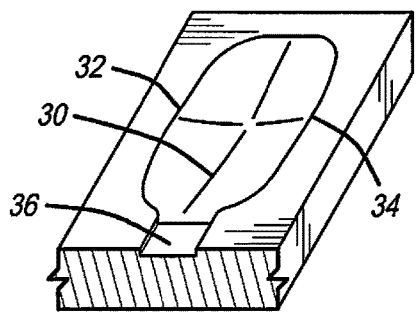
FIG. 3A—depicts a mold for forming the flexible circuit array in a curve. Progressively smaller molds are used to curve the array.
Figure 3B:
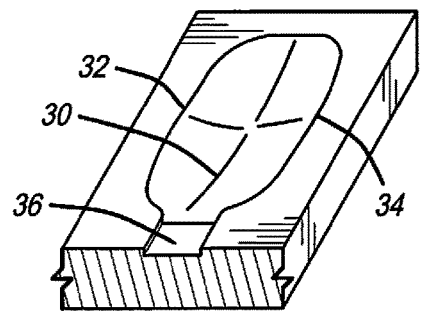
FIG. 3B depicts a smaller mold than FIG. 3A.
Figure 3C:
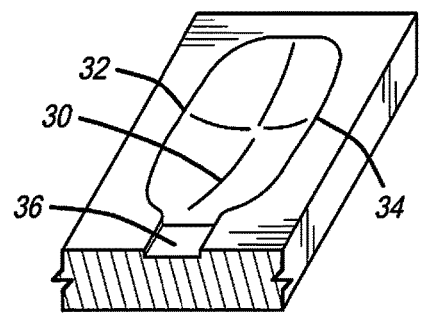
FIG. 3C depicts a smaller mold than FIG. 3B.
Figure 3D:
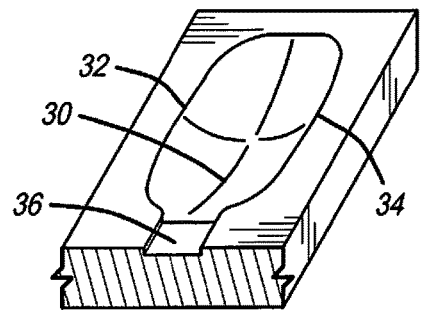
FIG. 3D depicts a smaller mold than FIG. 3C.
Figure 3E:
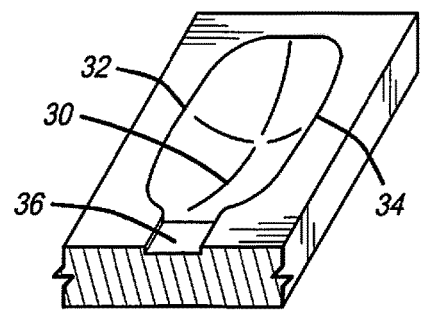
FIG. 3E depicts a smaller mold than FIG. 3D.

FIG. 2 shows a side view of the implanted portion of the retinal prosthesis, in particular, emphasizing the fan tail 24. When implanting the retinal prosthesis, it is necessary to pass the strap 22 under the eye muscles to surround the sclera. The secondary inductive coil 16 and molded body 18 must also follow the strap 22 under the lateral rectus muscle on the side of the sclera. The implanted portion of the retinal prosthesis is very delicate. It is easy to tear the molded body 18 or break wires in the secondary inductive coil 16. In order to allow the molded body 18 to slide smoothly under the lateral rectus muscle, the molded body 18 is shaped in the form of a fan tail 24 on the end opposite the electronics package 14.

The flexible circuit 1 is a made by the following process. First, a layer of polymer (such as polyimide, fluoro-polymers, silicone or other polymers) is applied to a support substrate (not part of the array) such as glass. Layers may be applied by spinning, meniscus coating, casting, sputtering, or other physical or chemical vapor deposition, or similar process. Subsequently, a metal layer is applied to the polymer. The metal is patterned by photolithographic process. Preferably, a photo-resist is applied and patterned by photolithography followed by a wet etch of the unprotected metal. Alternatively, the metal can be patterned by lift-off technique, laser ablation or applied by direct write techniques.

Then, the top layer of polymer is applied over the metal. It is advantageous to make this metal thicker at the electrode and bond pad to improve electrical continuity. This can be accomplished through any of the above methods, or electroplating before or after the said top layer of polymer is applied. Openings in the top layer for electrical contact to the electronics package 14 and the electrodes may be accomplished by laser ablation or reactive ion etching (RIE) or photolithography and wet etch. Making the electrode openings in the top layer smaller than the electrodes promotes adhesion by avoiding delaminating around the electrode edges.

The pressure applied against the retina by the flexible circuit electrode array is critical. Too little pressure causes increased electrical resistance between the array and retina. It should be noted that while the present invention is described in terms of application to the retina, the techniques described are equally applicable to many forms of neural stimulation. Application to the retina requires a convex spherical curve. Application to the cochlea requires a constant curve in one dimension and a spiral curve in the other. Application to the cerebral cortex requires a concave spherical curve. Cortical stimulation is useful for artificial vision or hearing, touch and motor control for limb prostheses, deep brain stimulation for Parkinson's disease and multiple sclerosis, and many other applications.

Common flexible circuit fabrication techniques such as photolithography generally require that a flexible circuit electrode array be made flat. Since the retina is spherical, a flat array will necessarily apply more pressure near its edges, than at its center. With most polymers, it is possible to curve them when heated in a mold. By applying the right amount of heat to a completed array, a curve can be induced that matches the curve of the retina. To minimize warping, it is often advantageous to repeatedly heat the flexible circuit in multiple molds, each with a decreasing radius. FIGS. 3A-3E illustrate a series of molds according to the preferred embodiment. Since the flexible circuit will maintain a constant length, the curvature must be slowly increased along that length. As the curvature 30 decreases in successive molds (FIGS. 3A-3E) the straight line length between ends 32 and 34, must decrease to keep the length along the curvature 30 constant, where mold 3E approximates the curvature of the retina or other desired neural tissue. The molds provide a further opening 36 for the flexible circuit cable 12 of the array to exit the mold without excessive curvature.

It should be noted that suitable polymers include thermoplastic materials and thermoset materials. While a thermoplastic material will provide some stretch when heated, a thermoset material will not. The successive molds are, therefore, advantageous only with a thermoplastic material. A thermoset material works as well in a single mold as it will with successive smaller molds. It should be noted that, particularly with a thermoset material, excessive curvature in three dimensions will cause the polymer material to wrinkle at the edges. This can cause damage to both the array and the retina. Hence, the amount of curvature is a compromise between the desired curvature, array surface area, and the properties of the material.

Figure 4A:
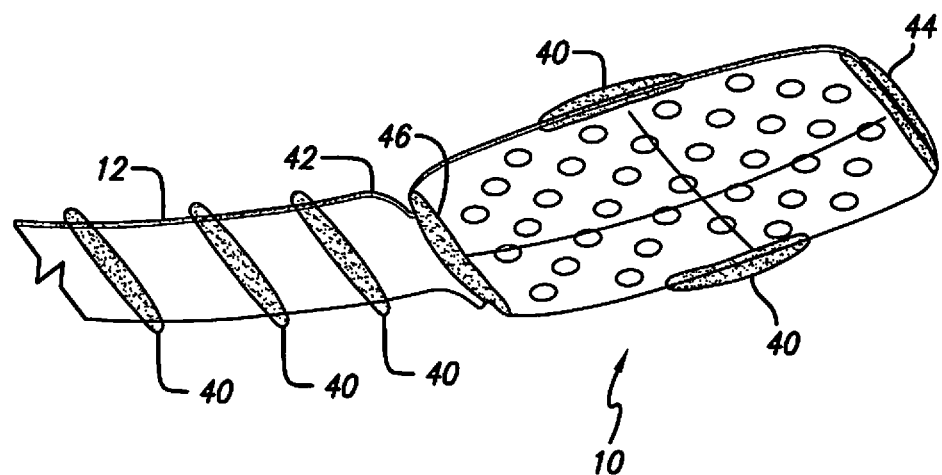
FIG. 4A depicts an alternate view of the invention with ribs to help maintain curvature and prevent retinal damage.
Figure 4B:
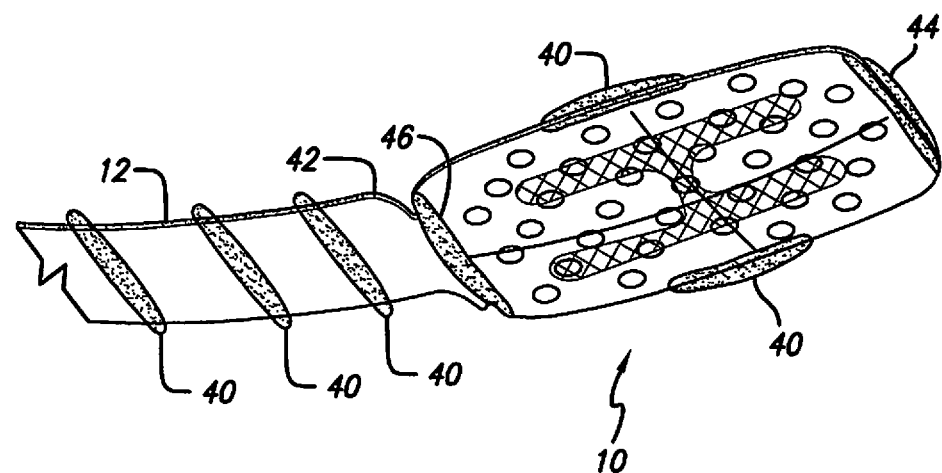
FIG. 4B depicts an alternate view of the invention with ribs to help maintain curvature and prevent retinal damage and a polymer support in the shape of H.

Referring to FIG. 4A and FIG. 4B, the edges of the polymer layers are often sharp. There is a risk that the sharp edges of a flexible circuit will cut into delicate retinal tissue. It is advantageous to add a soft material, such as silicone, to the edges of a flexible circuit electrode array to round the edges and protect the retina. Silicone around the entire edge may make the flexible circuit less flexible. So, it is advantageous to provide silicone bumpers or ribs to hold the edge of the flexible circuit electrode array away from the retinal tissue. Curvature 40 fits against the retina. The leading edge 44 is most likely to cause damage and is therefore fit with a molded silicone bumper. Also, edge 46, where the array lifts off the retina can cause damage and should be fit with a bumper. Any space along the side edges of curvature 40 may cause damage and may be fit with bumpers as well. It is also possible for the flexible circuit cable 12 of the electrode array to contact the retina. It is, therefore, advantageous to add periodic bumpers along the flexible circuit cable 12.

It is also advantageous to create a reverse curve or service loop in the flexible circuit cable 12 of the flexible circuit electrode array to gently lift the flexible circuit cable 12 off the retina and curve it away from the retina, before it pierces the sclera at a sclerotomy. It is not necessary to heat curve the service loop as described above, as the flexible circuit electrode array can simply be bent or creased upon implantation. This service loop reduces the likelihood of any stress exerted extraocularly from being transmitted to the electrode region and retina. It also provides for accommodation of a range of eye sizes.

With existing technology, it is necessary to place the implanted control electronics outside of the sclera, while a retinal flexible circuit electrode array must be inside the sclera in order to contact the retina. The sclera is cut through at the pars plana, forming a sclerotomy, and the flexible circuit passed through the sclerotomy. A flexible circuit is thin but wide. The more electrode wires, the wider the flexible circuit must be. It may be difficult to seal a sclerotomy over a flexible circuit wide enough to support enough wires for a high resolution array. A narrow sclerotomy is preferable.

Figure 5A:
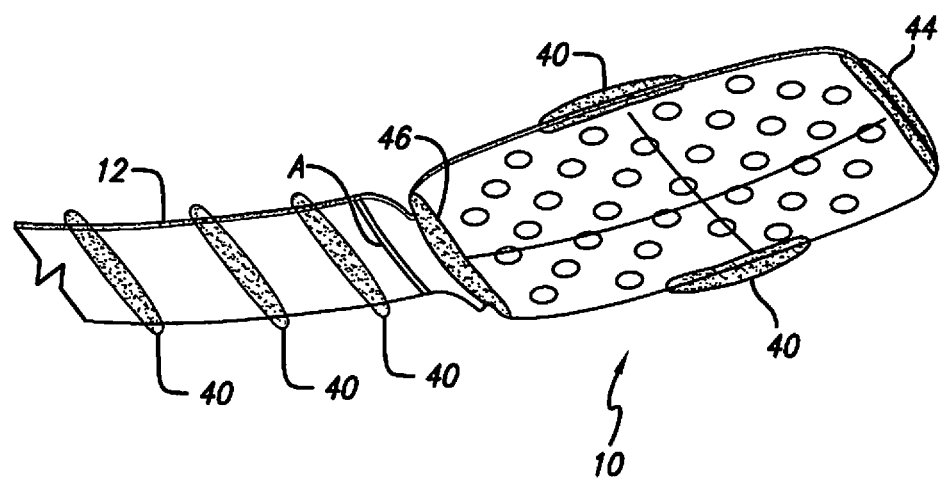
FIG. 5A depicts an alternate view of the invention with ribs to help maintain curvature and prevent retinal damage.
Figure 5B:
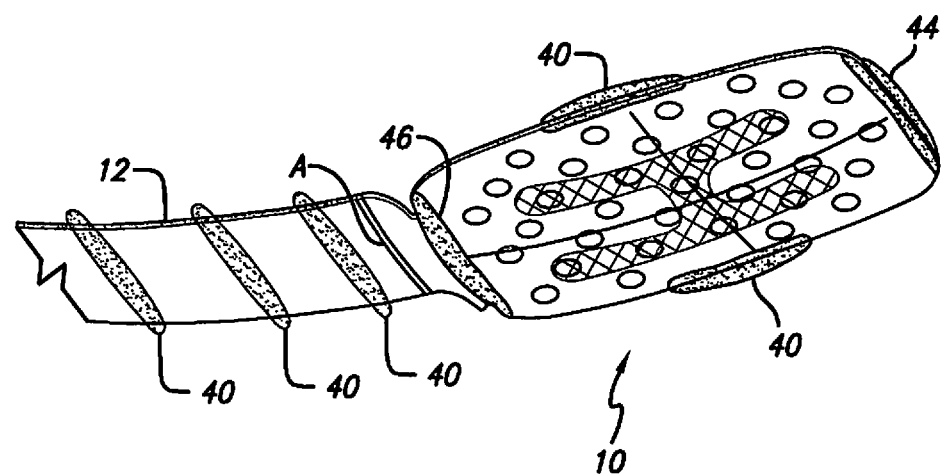
FIG. 5B depicts an alternate view of the invention with ribs to help maintain curvature and prevent retinal damage and a polymer support in the shape of H.

FIG. 5A and FIG. 5B depict a further embodiment of the part of the prosthesis shown in FIG. 4A and FIG. 4B with a fold A between the circuit electrode array 10 and the flexible circuit cable 12. The angle in the fold A, also called the ankle, has an angle of 1°-180°, preferably 80°-120°. The fold A is advantageous since it reduces tension and enables an effective attachment of the flexible electrode circuit array 10 to the retina.

Figure 6:
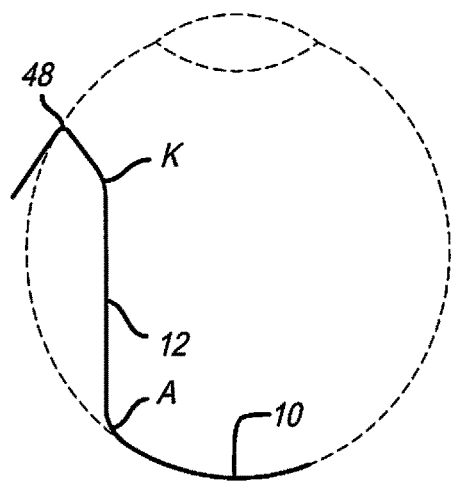
FIG. 6 depicts a cross-sectional view of the prosthesis shown inside of the eye with an angle in the flexible circuit cable at the sclerotomy and a fold between the circuit electrode region and the flexible circuit cable.

FIG. 6 depicts a side view of the prosthesis inside of the eye with an angle K of the flexible circuit cable 12 and a fold A between the circuit electrode array 10 and the flexible circuit cable 12. The angle K is about 45°-180° and preferably 80°-100°. The fold K, also called the knee, is advantageous because it decreases pressure which would be applied by the flexible circuit cable 10.

Figure 7:
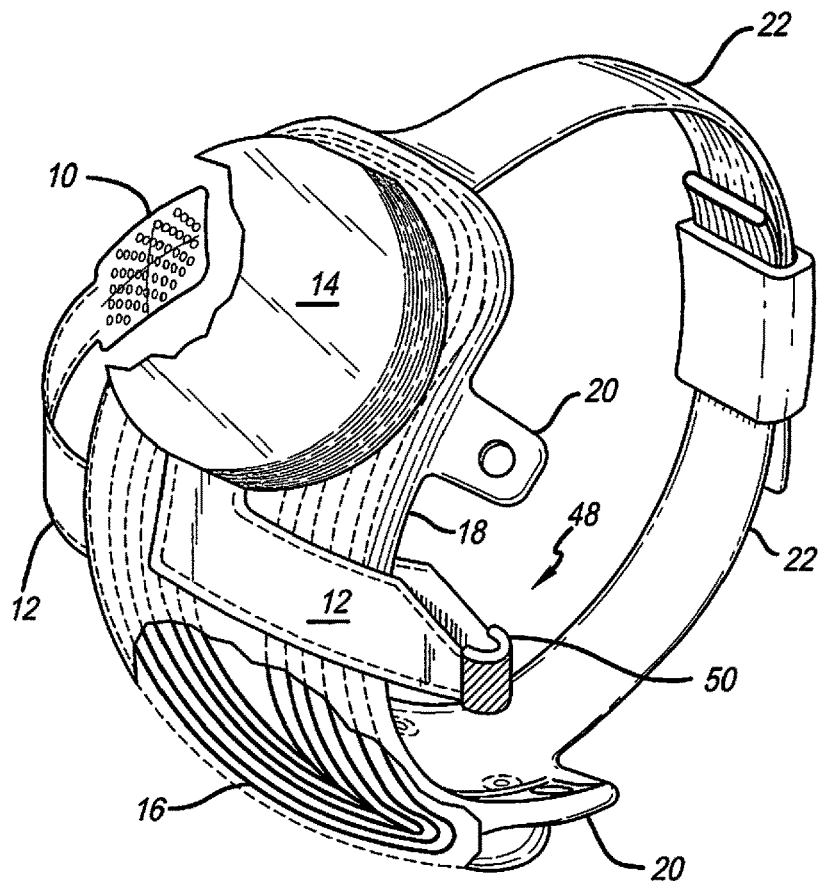
FIG. 7 depicts the implanted portion including a fold in the array to reduce the width at the sclerotomy and a sleeve to promote sealing of the sclerotomy.

FIG. 7 shows the implanted portion of the retinal prosthesis including the additional feature of a gentle twist or fold 48 in the flexible circuit cable 12, where the flexible circuit cable 12 passes through the sclera (sclerotomy). The twist may be a simple sharp twist, or fold 48; or it may be a longer twist, forming a tube. While the tube is rounder, it reduces the flexibility of the flexible circuit. A simple fold 48 reduces the width of the flexible circuit with only minimal impact on flexibility.

Further, silicone or other pliable substance may be used to fill the center of the tube or fold 48 formed by the twisted flexible circuit cable 12. Further, it is advantageous to provide a sleeve or coating 50 that promotes healing of the sclerotomy. Polymers such as polyimide, which may be used to form the flexible circuit cable 12 and flexible circuit electrode array 10, are generally very smooth and do not promote a good bond between the flexible circuit cable 12 and scleral tissue. A sleeve or coating of polyester, collagen, silicone, Gore-tex, or similar material would bond with scleral tissue and promote healing. In particular, a porous material will allow scleral tissue to grow into the pores promoting a good bond.

Alternatively, the flexible circuit electrode array 10 may be inserted through the sclera, behind the retina, and placed between the retina and choroid to stimulate the retina subretinally. In this case, it is advantageous to provide a widened portion, or stop, of the flexible circuit cable 12 to limit how far the flexible circuit electrode array is inserted and to limit the transmission of stress through the sclera. The stop may be widening of the flexible circuit 1 or it may be added material such as a bumper or sleeve.

Human vision provides a field of view that is wider than it is high. This is partially due to fact that we have two eyes, but even a single eye provides a field of view that is approximately 90° high and 140° to 160° degrees wide. It is therefore, advantageous to provide a flexible circuit electrode array 10 that is wider than it is tall. This is equally applicable to a cortical visual array. In which case, the wider dimension is not horizontal on the visual cortex, but corresponds to horizontal in the visual scene.

FIGS. 8A-8D show the flexible circuit electrode array prior to folding and attaching the array to the electronics package 14. At one end of the flexible circuit cable 12 is an interconnection pad 52 for connection to the electronics package 14. At the other end of the flexible circuit cable 12 is the flexible circuit electrode array 10. Further, an attachment point 54 is provided near the flexible circuit electrode array 10. A retina tack (not shown) is placed through the attachment point 54 to hold the flexible circuit electrode array 10 to the retina. A stress relief 55 is provided surrounding the attachment point 54. The stress relief 55 may be made of a softer polymer than the flexible circuit, or it may include cutouts or thinning of the polymer to reduce the stress transmitted from the retina tack to the flexible circuit electrode array 10. The flexible circuit cable 12 is formed in a dog leg pattern so than when it is folded at fold 48 it effectively forms a straight flexible circuit cable 12 with a narrower portion at the fold 48 for passing through the sclerotomy.

FIGS. 9A-9D show the flexible circuit electrode array after the flexible circuit cable 12 is folded at the fold 48 to form a narrowed section. The flexible circuit cable 12 may include a twist or tube shape as well. With a retinal prosthesis as shown in FIG. 1, the bond pad 52 for connection to the electronics package 14 and the flexible circuit electrode array 10 are on opposite sides of the flexible circuit. This requires patterning, in some manner, of both the base polymer layer and the top polymer layer. By folding the flexible circuit cable 12 of the flexible circuit electrode array 10, the openings for the bond pad 52 and the electrodes are on the top polymer layer and only the top polymer layer needs to be patterned.

Also, since the narrowed portion of the flexible circuit cable 12 pierces the sclera, shoulders formed by opposite ends of the narrowed portion help prevent the flexible circuit cable 12 from moving through the sclera. It may be further advantageous to add ribs or bumps of silicone or similar material to the shoulders to further prevent the flexible circuit cable 12 from moving through the sclera.

Further it is advantageous to provide a suture tab 56 in the flexible circuit body near the electronics package to prevent any movement in the electronics package from being transmitted to the flexible circuit electrode array 10. Alternatively, a segment of the flexible circuit cable 12 can be reinforced to permit it to be secured directly with a suture.

An alternative to the bumpers described in FIG. 4A, is a skirt of silicone or other pliable material as shown in FIGS. 11, 12, 13 and 14. A skirt 60 covers the flexible circuit electrode array 10, and extends beyond its edges. It is further advantageous to include wings 62 adjacent to the attachment point 54 to spread any stress of attachment over a larger area of the retina. There are several ways of forming and bonding the skirt 60. The skirt 60 may be directly bonded through surface activation, indirectly bonded using an adhesive, or molded over the flexible circuit electrode array.

Alternatively, a flexible circuit electrode array 10 may be layered using different polymers for each layer. Using too soft of a polymer may allow too much stretch and break the metal traces. Too hard of a polymer may cause damage to delicate neural tissue. Hence a relatively hard polymer, such as polyimide, may be used for the bottom layer and a relatively softer polymer such as silicone, may be used for the top layer, including an integral skirt to protect delicate neural tissue.

Figure 11:
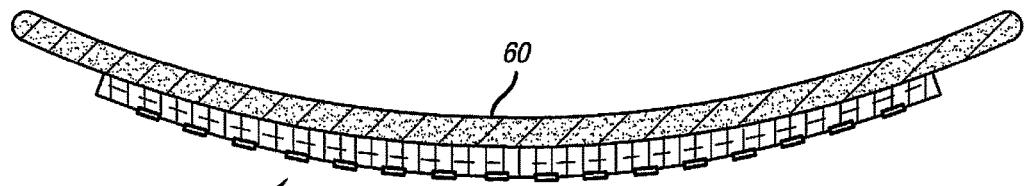
FIG. 11 depicts a flexible circuit array with a protective skirt bonded to the back side of the flexible circuit array.
Figure 12:
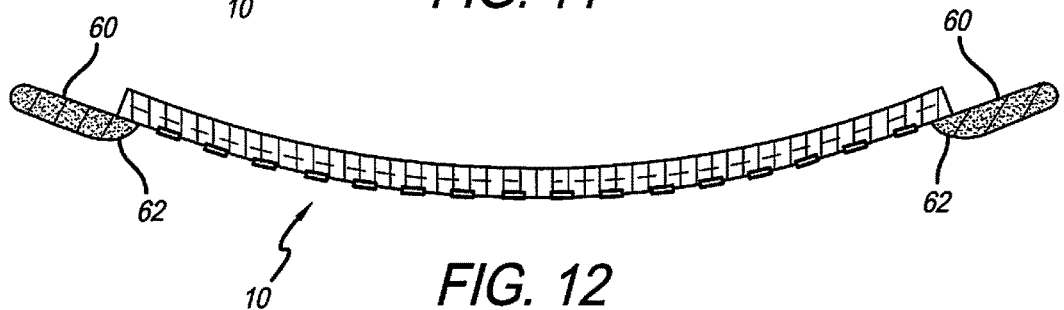
FIG. 12 depicts a flexible circuit array with a protective skirt bonded to the front side of the flexible circuit array.

The simplest solution is to bond the skirt 60 to the back side (away from the retina) of the flexible circuit electrode array 10 as shown in FIG. 11. While this is the simplest mechanical solution, sharp edges of the flexible circuit electrode array 10 may contact the delicate retina tissue. Bonding the skirt to the front side (toward the retina) of the flexible circuit electrode array 10, as shown in FIG. 12, will protect the retina from sharp edges of the flexible circuit electrode array 10. However, a window 62 must be cut in the skirt 60 around the electrodes. Further, it is more difficult to reliably bond the skirt 60 to the flexible circuit electrode array 10 with such a small contact area. This method also creates a space between the electrodes and the retina which will reduce efficiency and broaden the electrical field distribution of each electrode. Broadening the electric field distribution will limit the possible resolution of the flexible circuit electrode array 10.

Figure 13:
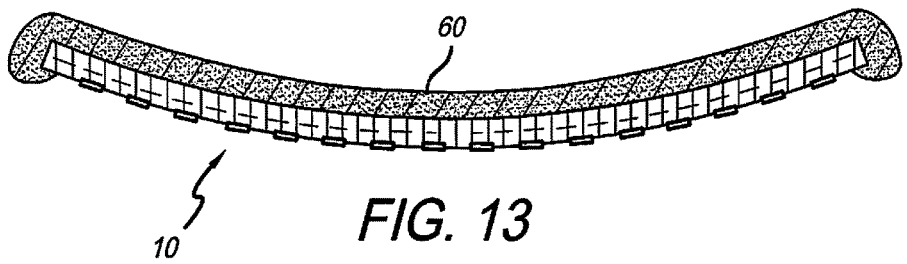
FIG. 13 depicts a flexible circuit array with a protective skirt bonded to the back side of the flexible circuit array and molded around the edges of the flexible circuit array.

FIG. 13 shows another structure where the skirt 60 is bonded to the back side of the flexible circuit electrode array 10, but curves around any sharp edges of the flexible circuit electrode array 10 to protect the retina. This gives a strong bond and protects the flexible circuit electrode array 10 edges. Because it is bonded to the back side and molded around the edges, rather than bonded to the front side of the flexible circuit electrode array 10, the portion extending beyond the front side of the flexible circuit electrode array 10 can be much smaller. This limits any additional spacing between the electrodes and the retinal tissue.

Figure 14:
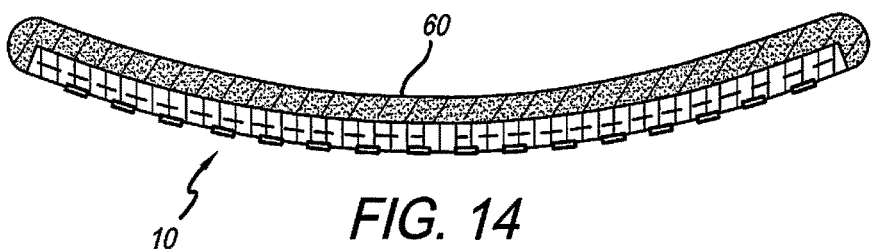
FIG. 14 depicts a flexible circuit array with a protective skirt bonded to the back side of the flexible circuit array and molded around the edges of the flexible circuit array and flush with the front side of the array.

FIG. 14 shows a flexible circuit electrode array 10 similar to FIG. 13, with the skirt 60, flush with the front side of the flexible circuit electrode array 10 rather than extending beyond the front side. While this is more difficult to manufacture, it does not lift the electrodes off the retinal surface as with the array in FIG. 10A. It should be noted that FIGS. 11, 13, and 14 show skirt 60 material along the back of the flexible circuit electrode array 10 that is not necessary other than for bonding purposes. If there is sufficient bond with the flexible circuit electrode array 10, it may be advantageous to thin or remove portions of the skirt 60 material for weight reduction.

Figure 15:
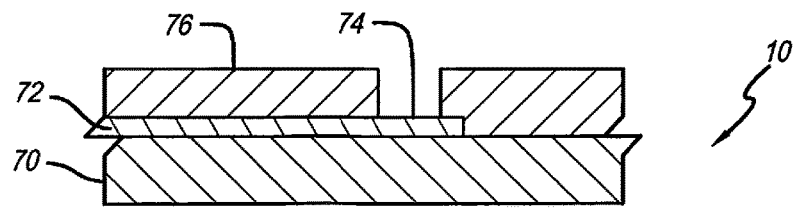
FIG. 15 is an enlarged view of a single electrode within the flexible circuit electrode array.

Referring to FIG. 15, the flexible circuit electrode array 10 is manufactured in layers. A base layer of polymer 70 is laid down, commonly by some form of chemical vapor deposition, spinning, meniscus coating, or casting. A layer of metal 72 (preferably platinum) is applied to the polymer base layer 70 and patterned to create electrodes 74 and traces for those electrodes. Patterning is commonly done by photolithographic methods. The electrodes 74 may be built up by electroplating or similar method to increase the surface area of the electrode 74 and to allow for some reduction in the electrodes 74 over time. Similar plating may also be applied to the bond pads 52 (FIGS. 8-10). A top polymer layer 76 is applied over the metal layer 72 and patterned to leave openings for the electrodes 74, or openings are created later by means such as laser ablation. It is advantageous to allow an overlap of the top polymer layer 76 over the electrodes 74 to promote better adhesion between the layers, and to avoid increased electrode reduction along their edges. The overlapping top layer promotes adhesion by forming a clamp to hold the metal electrode between the two polymer layers. Alternatively, multiple alternating layers of metal and polymer may be applied to obtain more metal traces within a given width.

FIGS. 16A-16D depict the flexible circuit array 12 before it is folded and attached to the implanted portion containing an additional fold A between the flexible electrode array 12 and the flexible cable 10. The angle in the fold A, also called the ankle, has an angle of 1°-180°, preferably 80°-120°. The ankle is advantageous in the process of inserting the prostheses in the eye and attaching it to the retina.

Figure 8A:
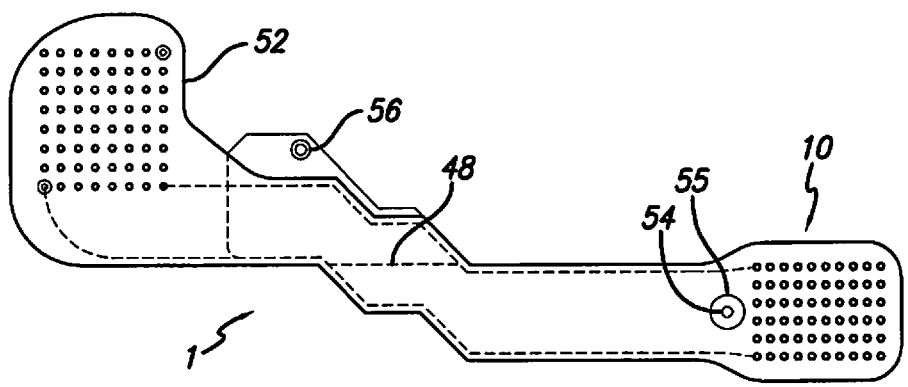
FIG. 8A depicts the flexible circuit array before it is folded and attached to the implanted portion.
Figure 8B:
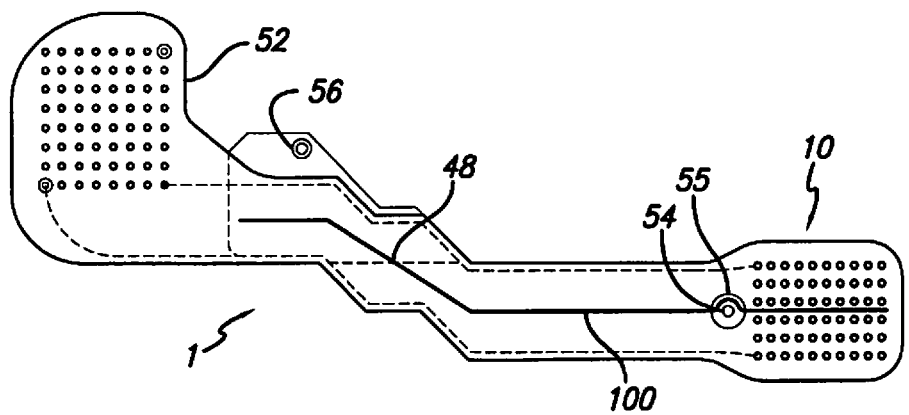
FIG. 8B depicts the flexible circuit array before it is folded and attached to the implanted portion with a wire.
Figure 8C:
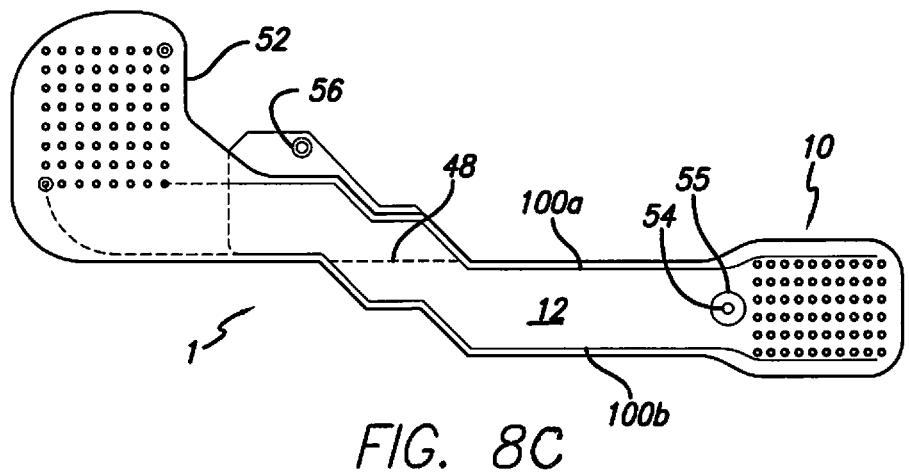
FIG. 8C depicts the flexible circuit array before it is folded and attached to the implanted portion with two wires.
Figure 8D:
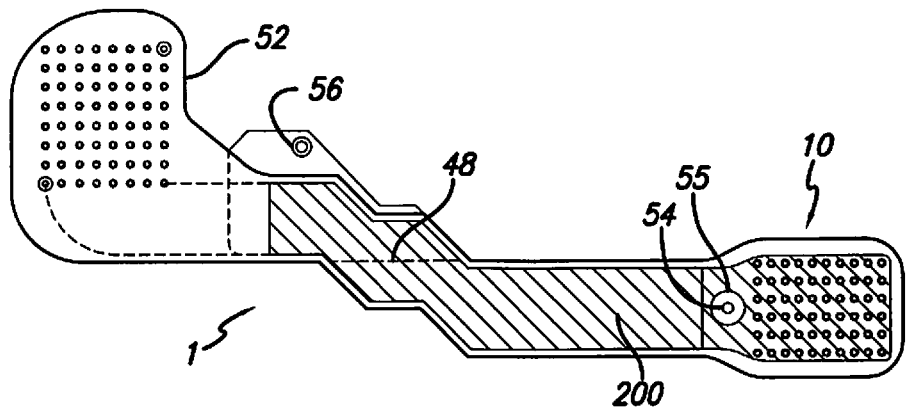
FIG. 8D depicts the flexible circuit array before it is folded and attached to the implanted portion with a film or foil.
Figure 9A:
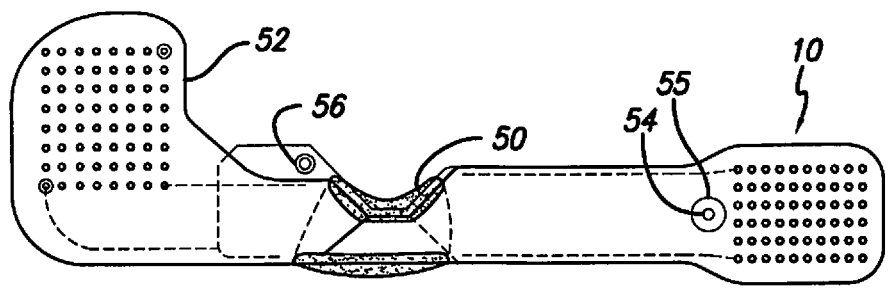
FIG. 9A depicts the flexible circuit array folded.
Figure 9B:
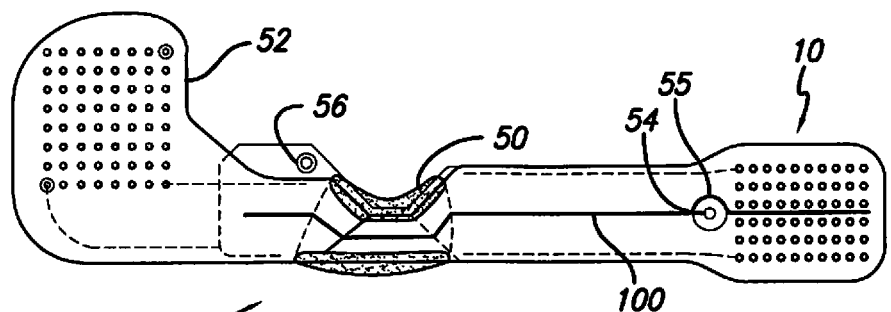
FIG. 9B depicts the flexible circuit array folded with a wire.
Figure 9C:
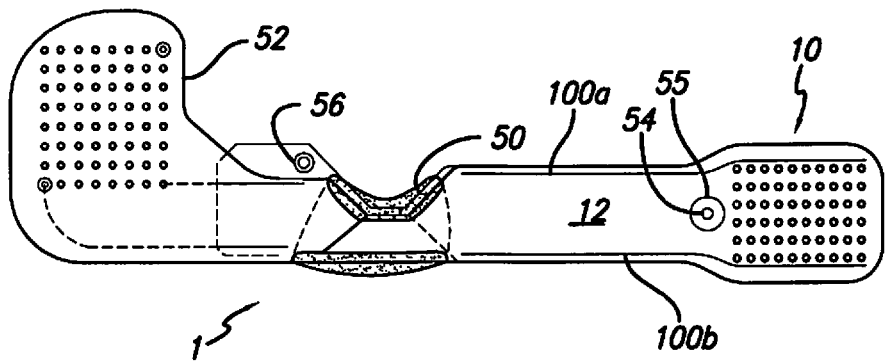
FIG. 9C depicts the flexible circuit array folded with two wires.
Figure 9D:
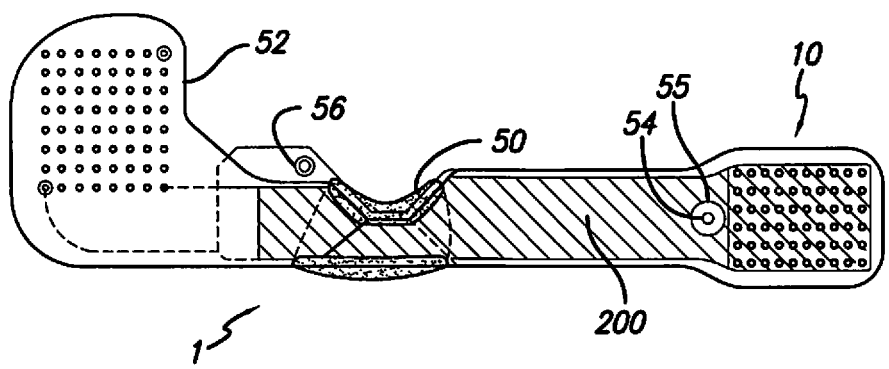
FIG. 9D depicts the flexible circuit array folded with a film or foil.
Figure 16A:
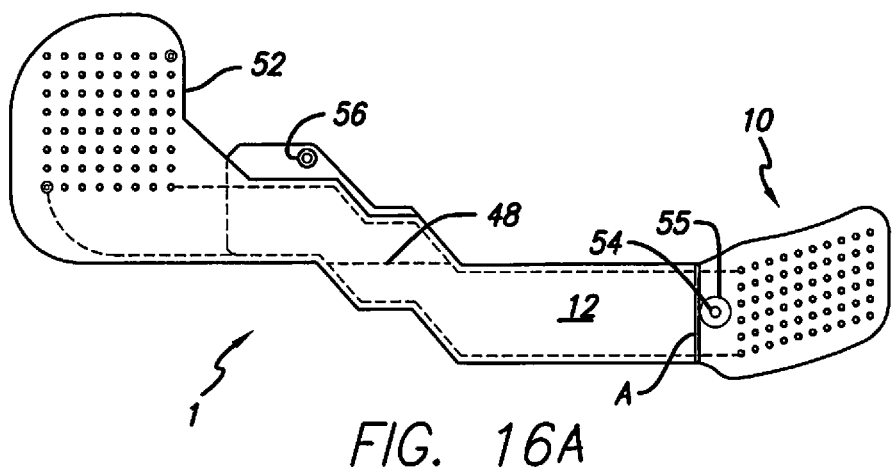
FIG. 16A depicts the flexible circuit array before it is folded and attached to the implanted portion containing an additional fold between the flexible electrode array and the flexible cable.
Figure 16B:
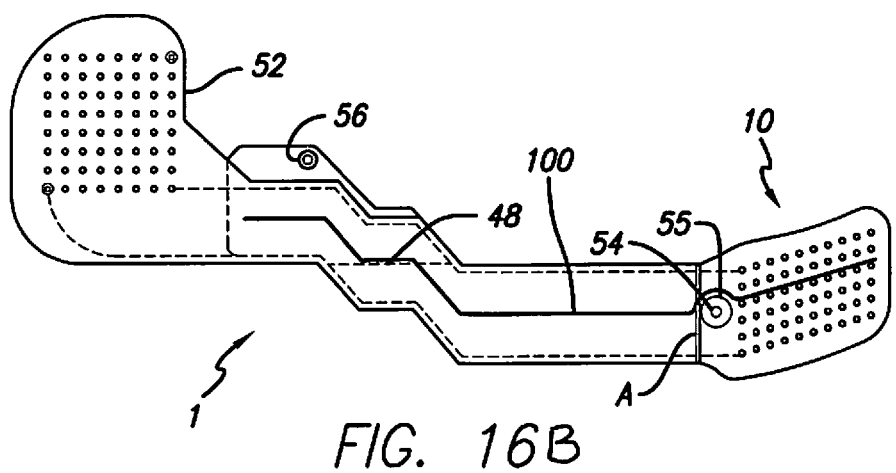
FIG. 16B depicts the flexible circuit array before it is folded and attached to the implanted portion containing an additional fold between the flexible electrode array and the flexible cable with a wire.
Figure 16C:
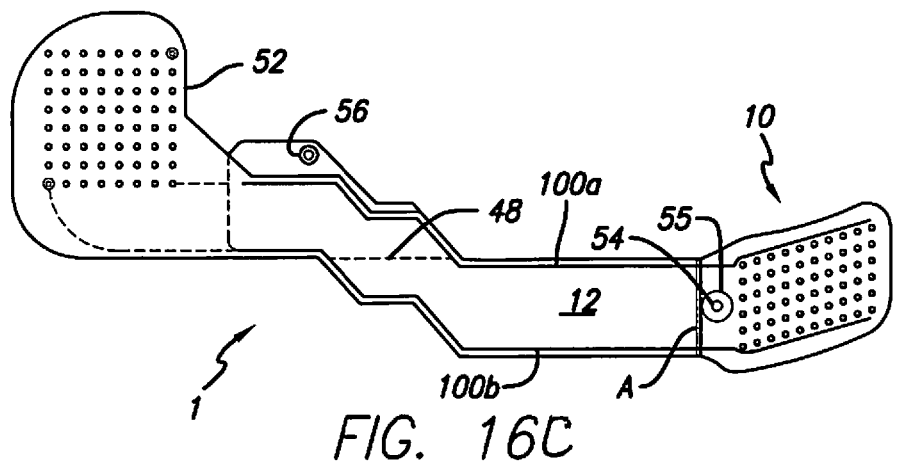
FIG. 16C depicts the flexible circuit array before it is folded and attached to the implanted portion containing an additional fold between the flexible electrode array and the flexible cable with two wires.
Figure 16D:
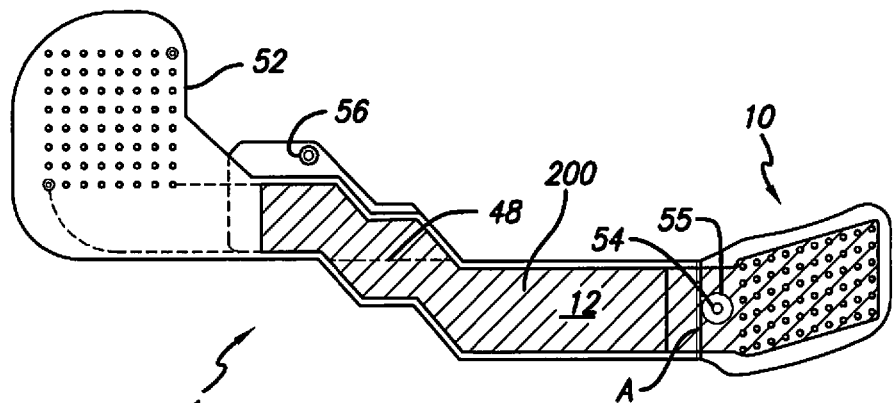
FIG. 16D depicts the flexible circuit array before it is folded and attached to the implanted portion containing an additional fold between the flexible electrode array and the flexible cable with a film or foil.

FIGS. 17A-17D depict the flexible circuit array 12 of FIG. 16A folded containing an additional fold A between the flexible electrode array 12 and the flexible cable 10. The flexible circuit array as shown in FIGS. 8A and 16A differ by the fold A from each other.

Figure 17A:
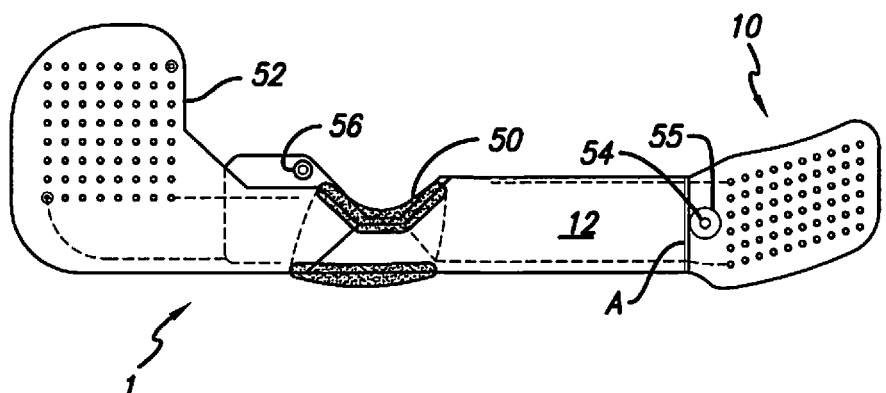
FIG. 17A depicts the flexible circuit array of FIG. 16 folded containing an additional fold between the flexible electrode array and the flexible cable.
Figure 17B:
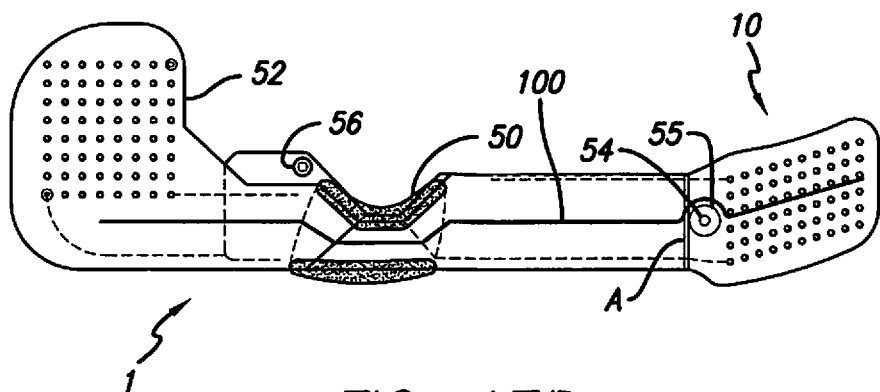
FIG. 17B depicts the flexible circuit array of FIG. 16 folded containing an additional fold between the flexible electrode array and the flexible cable with a wire.
Figure 17C:
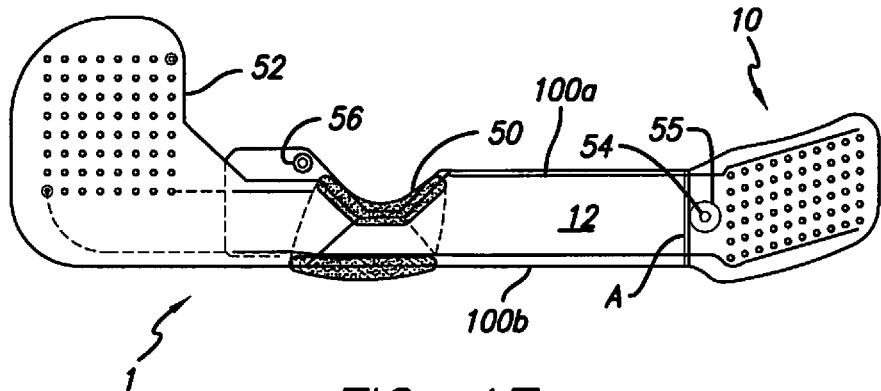
FIG. 17C depicts the flexible circuit array of FIG. 16 folded containing an additional fold between the flexible electrode array and the flexible cable with two wires.
Figure 17D:
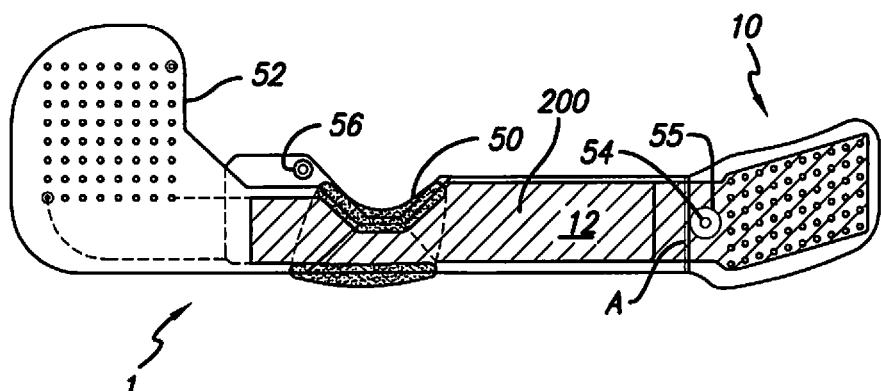
FIG. 17D depicts the flexible circuit array of FIG. 16 folded containing an additional fold between the flexible electrode array and the flexible cable with a film or foil.
Figure 18A:
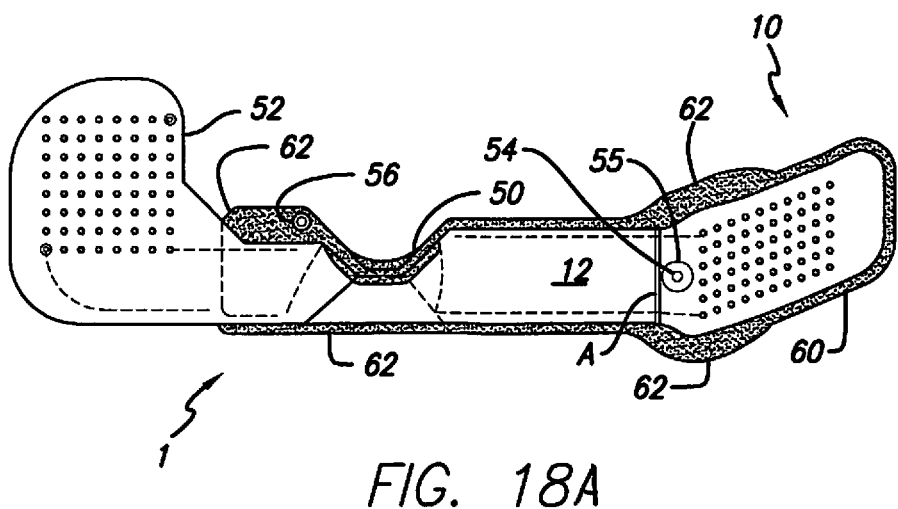
FIG. 18A depicts a flexible circuit array of FIG. 17A with a protective skirt and containing an additional fold between the flexible electrode array and the flexible cable.
Figure 18B:
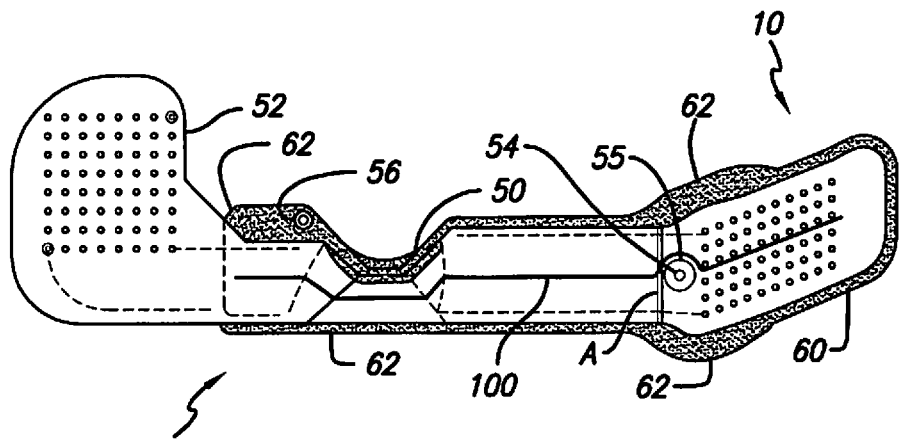
FIG. 18B depicts a flexible circuit array of FIG. 17A with a protective skirt and containing an additional fold between the flexible electrode array and the flexible cable with a wire.
Figure 18C:
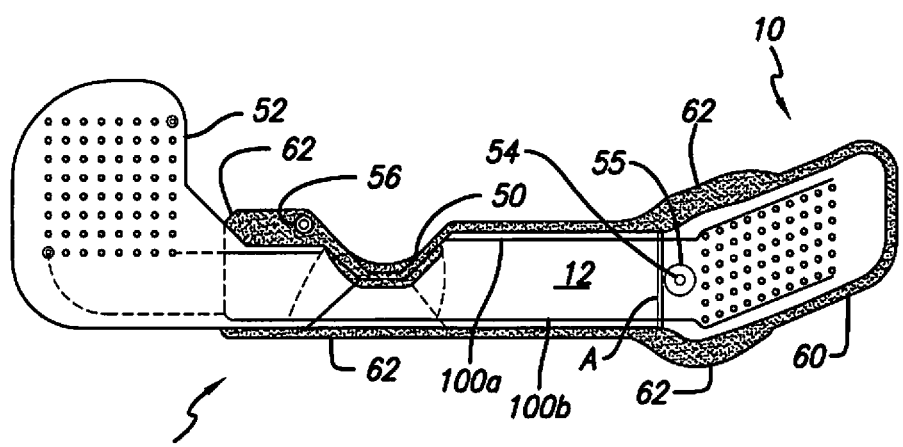
FIG. 18C depicts a flexible circuit array of FIG. 17A with a protective skirt and containing an additional fold between the flexible electrode array and the flexible cable with two wires.
Figure 18D:
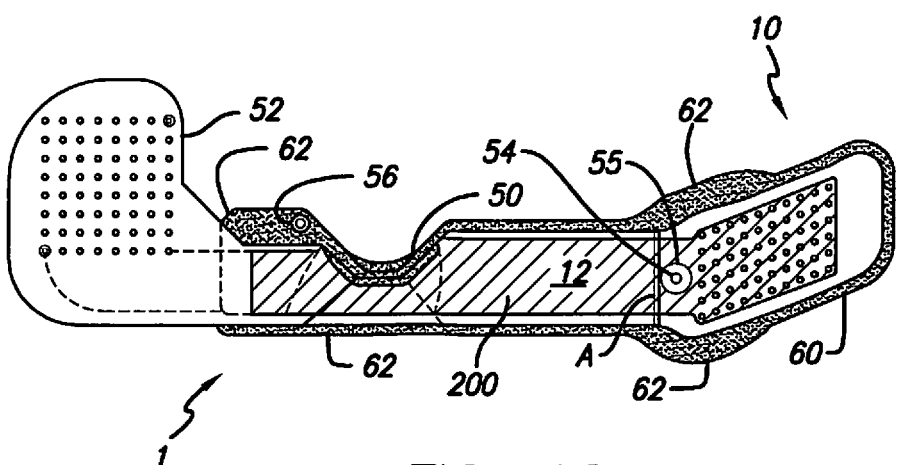
FIG. 18D depicts a flexible circuit array of FIG. 17A with a protective skirt and containing an additional fold between the flexible electrode array and the flexible cable with a film or foil.
Figure 20A:
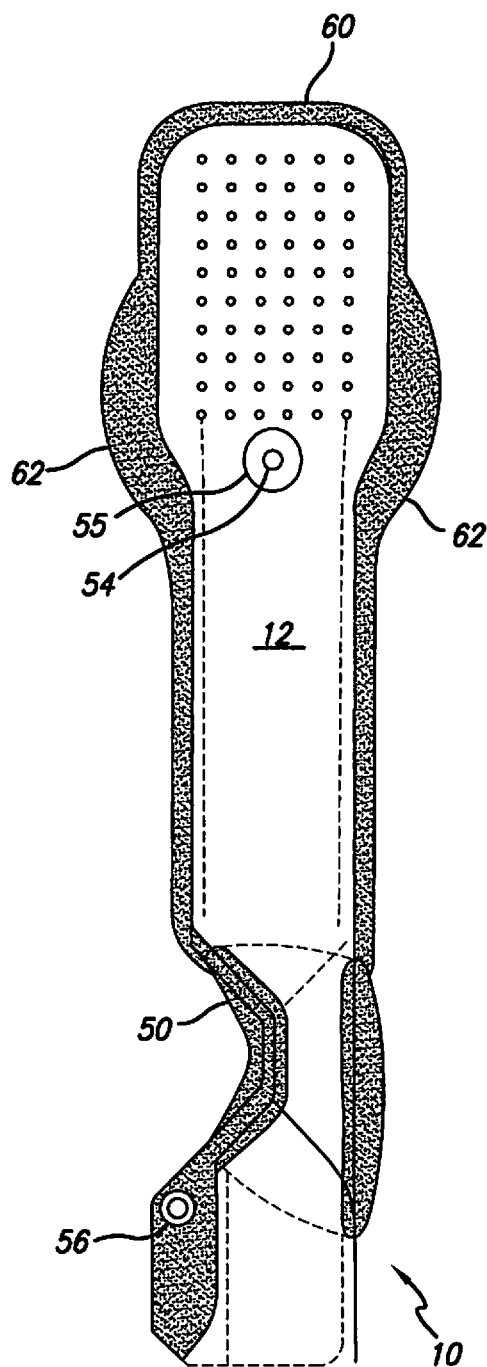
FIG. 20A depicts another variation without the horizontal angle between the flexible electrode array and the flexible cable but with an orientation of the electrodes in the flexible electrode array as shown for the variation in FIG. 19A.
Figure 20B:
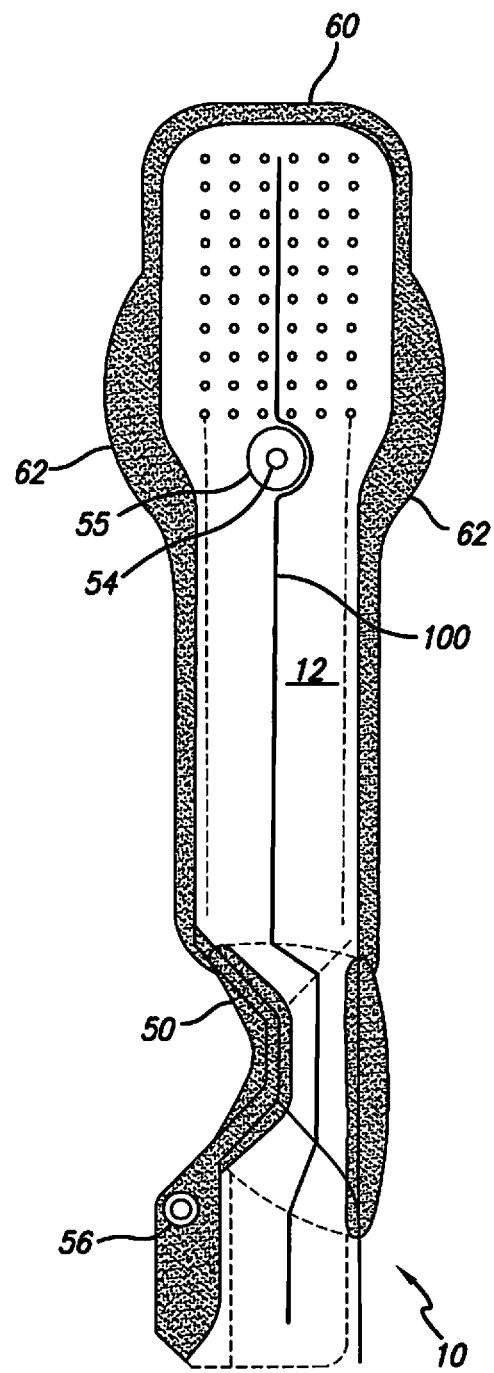
FIG. 20B depicts another variation without the horizontal angle between the flexible electrode array and the flexible cable but with an orientation of the electrodes in the flexible electrode array as shown for the variation in FIG. 19A with a wire.
Figure 21A:
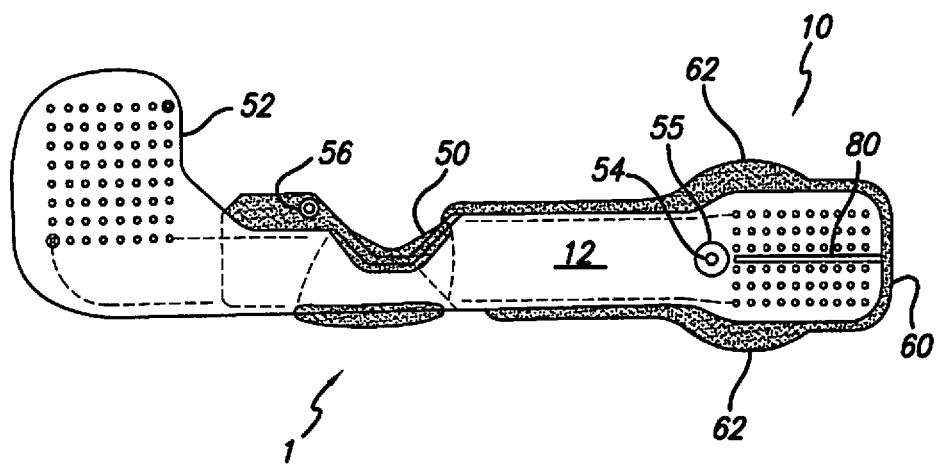
FIG. 21A depicts a top view of a flexible circuit array and flexible circuit cable wherein the array contains a slit along the length axis.
Figure 21B:
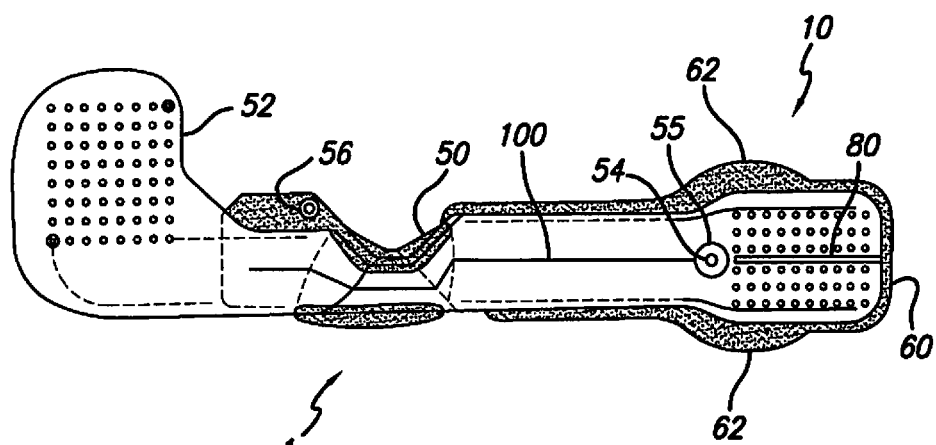
FIG. 21B depicts a top view of a flexible circuit array and flexible circuit cable wherein the array contains a slit along the length axis with a wire.
Figure 21C:
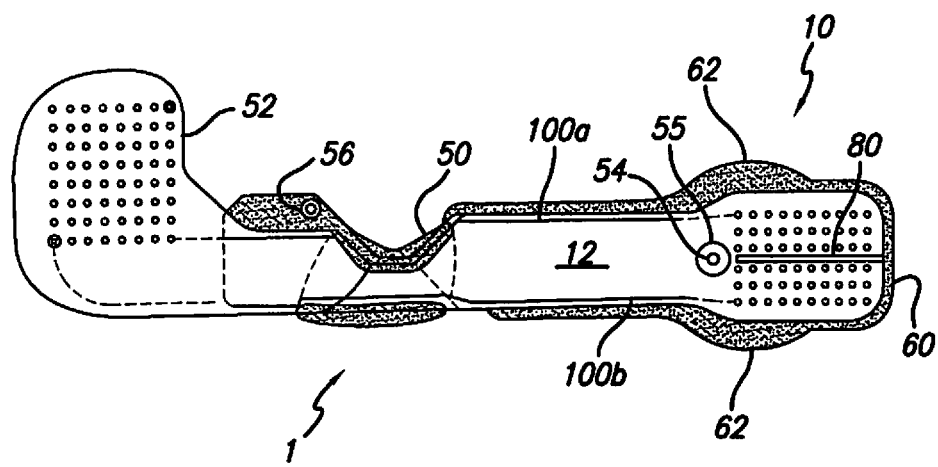
FIG. 21C depicts a top view of a flexible circuit array and flexible circuit cable wherein the array contains a slit along the length axis with two wires.
Figure 21D:
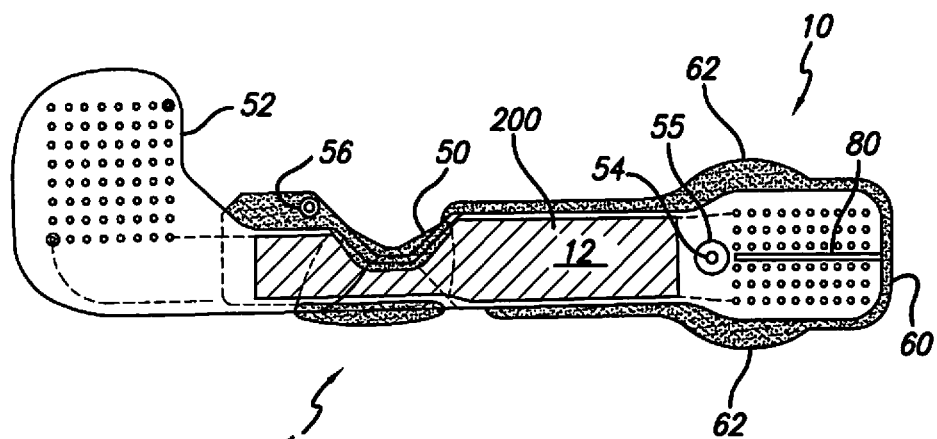
FIG. 21D depicts a top view of a flexible circuit array and flexible circuit cable wherein the array contains a slit along the length axis with a film or foil.
Figure 22A:
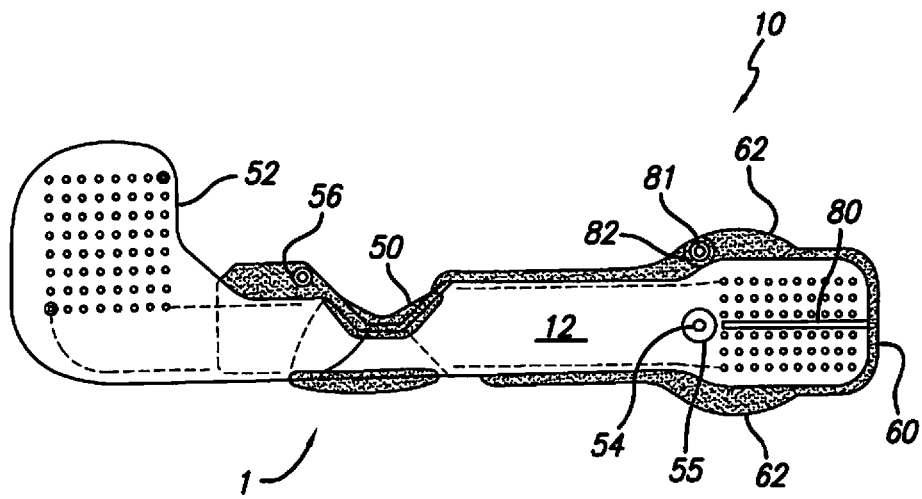
FIG. 22A depicts a top view of a flexible circuit array and flexible circuit cable wherein the array contains a slit along the length axis with a two attachment points.
Figure 22B:
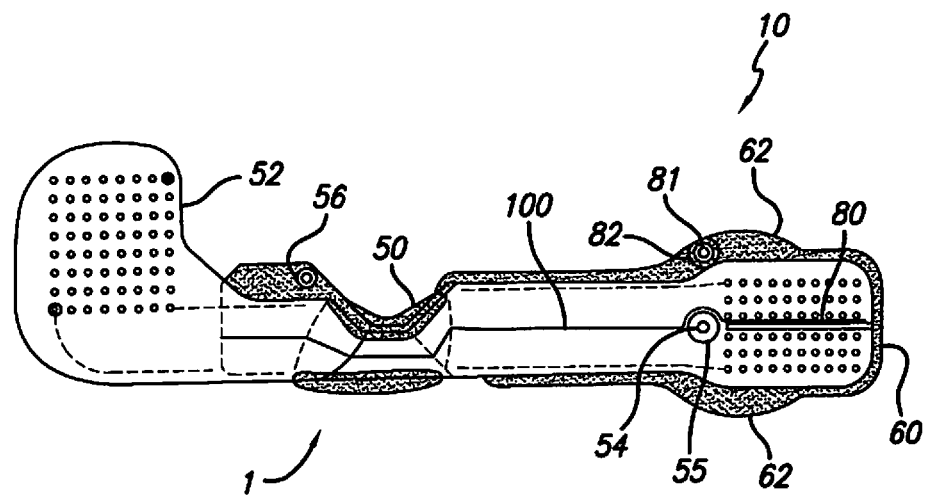
FIG. 22B depicts a top view of a flexible circuit array and flexible circuit cable wherein the array contains a slit along the length axis with a two attachment points with a wire.
Figure 22C:
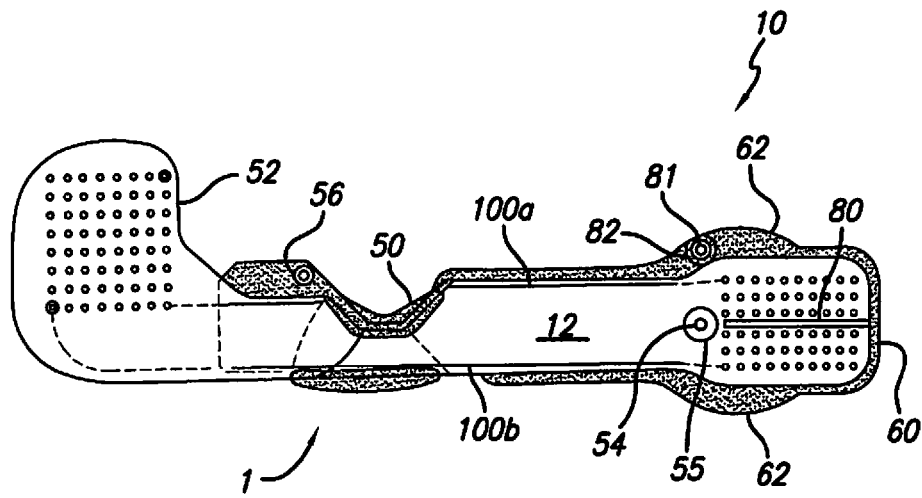
FIG. 22C depicts a top view of a flexible circuit array and flexible circuit cable wherein the array contains a slit along the length axis with a two attachment points with two wires.
Figure 22D:
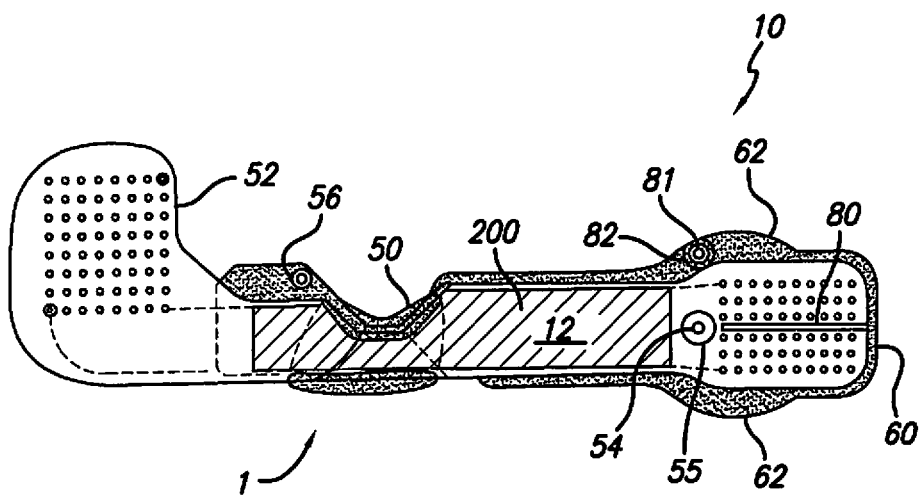
FIG. 22D depicts a top view of a flexible circuit array and flexible circuit cable wherein the array contains a slit along the length axis with a two attachment points with a film or foil.

FIGS. 18A-18D depict a flexible circuit array of FIG. 17A with a protective skirt 60 and containing an additional fold A between the flexible electrode array and the flexible cable. The flexible circuit array as shown in FIGS. 10A and 18A differ by the fold A from each other.

FIG. 19A depicts a top view of a flexible circuit array and flexible circuit cable. FIG. 19B depicts a top view of a flexible circuit array and flexible circuit cable showing the additional horizontal angle H between the flexible electrode array 12 and the flexible cable 10. The angle H is from about 1° to about 90° and preferably from about 30° to about 60°.

FIGS. 20A-20D depict another variation without the horizontal angle H between the flexible electrode array 12 and the flexible cable 10 but with an orientation of the electrodes in the flexible electrode array 12 as shown in FIG. 19A for a flexible electrode array 12. Both variations shown in FIGS. 19B and 20A have the advantage that the electrodes are oriented horizontally if they are inserted into the eye.

Figure 10A:
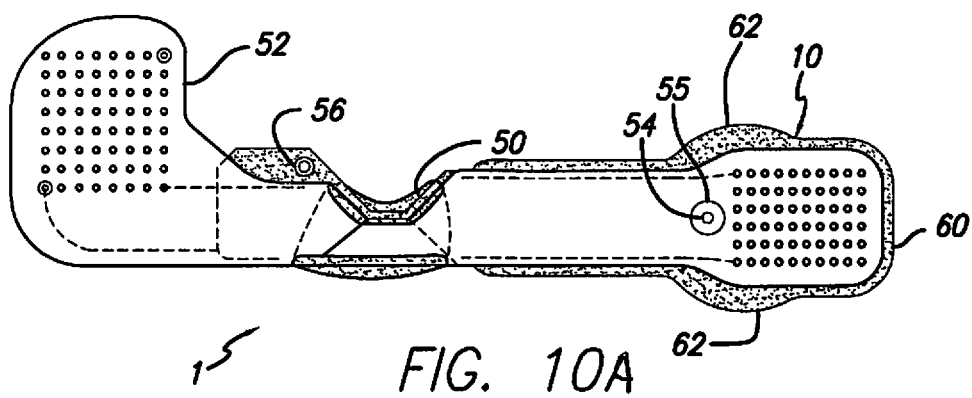
FIG. 10A depicts a flexible circuit array with a protective skirt.
Figure 10B:
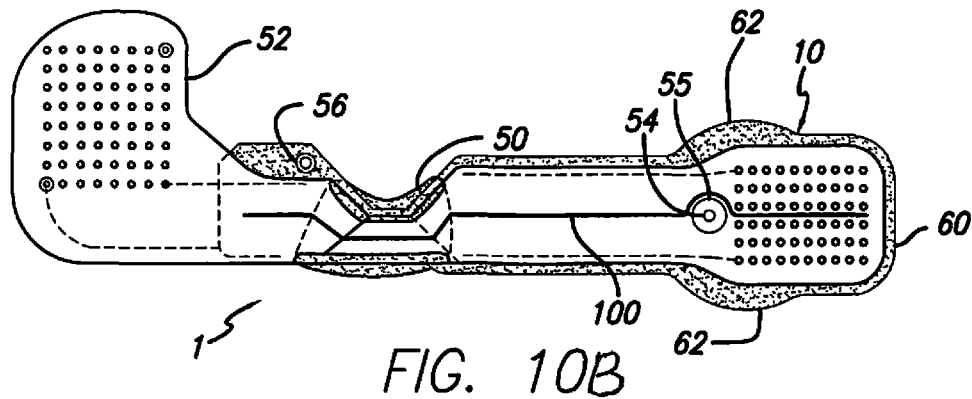
FIG. 10B depicts a flexible circuit array with a protective skirt with a wire.
Figure 10C:
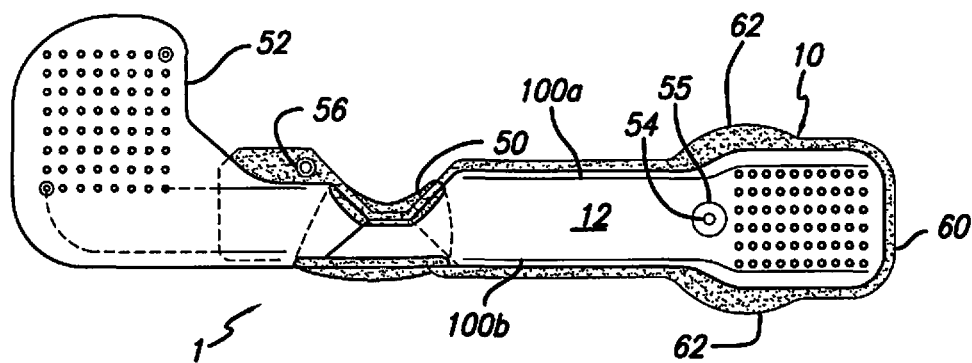
FIG. 10C depicts a flexible circuit array with a protective skirt with two wires.
Figure 10D:
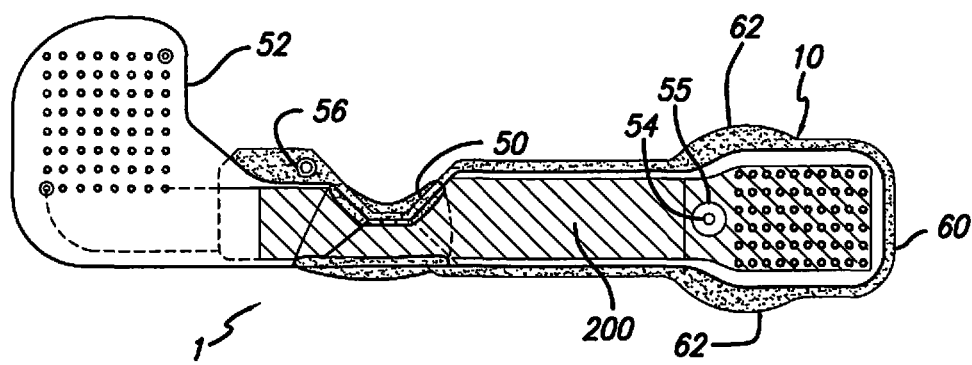
FIG. 10D depicts a flexible circuit array with a protective skirt with a film or foil.

FIGS. 21A-21D depict a top view of a flexible circuit array and flexible circuit cable as shown in FIGS. 10A and 18A wherein the array contains a slit along the length axis.

FIGS. 22A-22D depict a skirt of silicone or other pliable material as shown in FIG. 10A to 14. A skirt 60 covers the flexible circuit electrode array 10, and extends beyond its edges. In this embodiment of the present invention the flexible circuit electrode array contains a slit 80 along the lengths axis. Further, according to this embodiment, the skirt of silicone or other pliable material contains preferably at least two attachment points 81, and stress reliefs 82 are provided surrounding the attachment points 81. The attachment points 81 are located preferably on the skirt 60 outside the flexible circuit electrode 10 and are positioned apart as far as possible from each other. The two tacks 81 are far enough apart not to cause tenting, therefore fibrosis, between the two tacks, which causes a traction detachment of the retina. Furthermore, the polyimide is completely between the two tacks, which also reduces the possibility of tenting. Also, this orientation of tacks keeps the tacks away from the axons, which arise from the ganglion cells which are tried to be activated. They are away from the raffe. The wings act like external tabs or strain reliefs. The multiple tacks prevent rotation of the array.

The stress relief 82 may be made of a softer polymer than the flexible circuit, or it may include cutouts or thinning of the polymer to reduce the stress transmitted from the retina tack to the flexible circuit electrode array 10.

Figure 23:
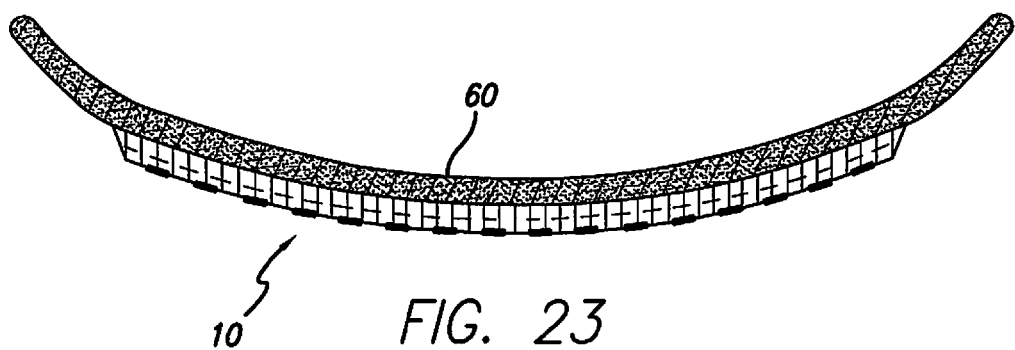
FIG. 23 depicts a flexible circuit array with a protective skirt bonded to the back side of the flexible circuit array with a progressively decreasing radius.

FIG. 23 depicts a flexible circuit array 10 with a protective skirt 60 bonded to the back side of the flexible circuit array 10 with a progressively decreasing radius. This variation shows an angle x grater than 90°. This angle is due to laser cutting. The laser cuts the polymer with an angle x. This leaves a sharp edge y. To avoid that the sharp edge comes into contact with the retina, the polyimide layer is turned around after the laser cutting and attached upsidedown to the skirt.

Figure 24:
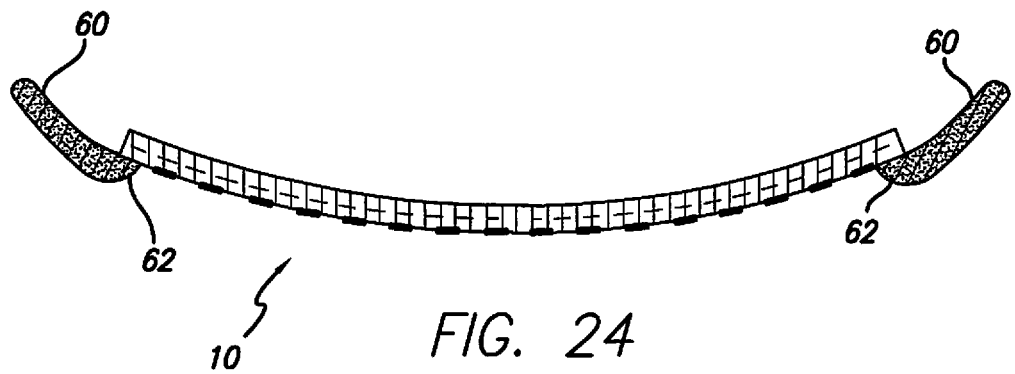
FIG. 24 depicts a flexible circuit array with a protective skirt bonded to the front side of the flexible circuit array with a progressively decreasing radius.

FIG. 24 depicts a flexible circuit array 10 with a protective skirt 60 bonded to the front side of the flexible circuit array 10 with a progressively decreasing radius.

Figure 25:
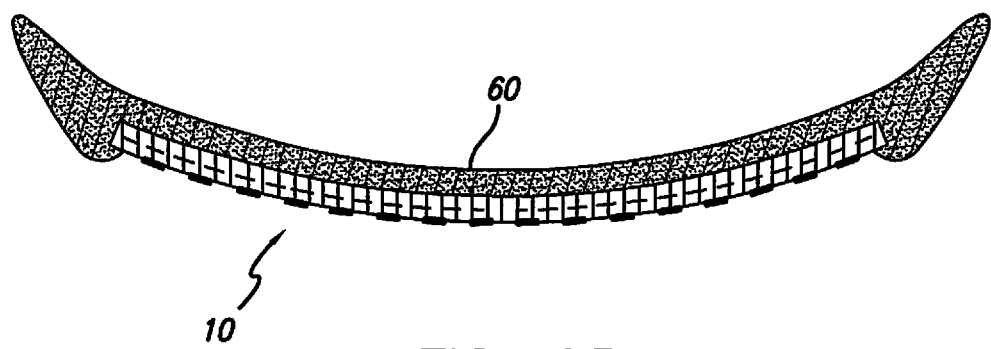
FIG. 25 depicts a flexible circuit array with a protective skirt bonded to the back side of the flexible circuit array and molded around the edges of the flexible circuit array with a progressively decreasing radius.

FIG. 25 depicts a flexible circuit array 10 with a protective skirt 60 bonded to the back side of the flexible circuit array 10 and molded around the edges of the flexible circuit array with a progressively decreasing radius.

Figure 26:
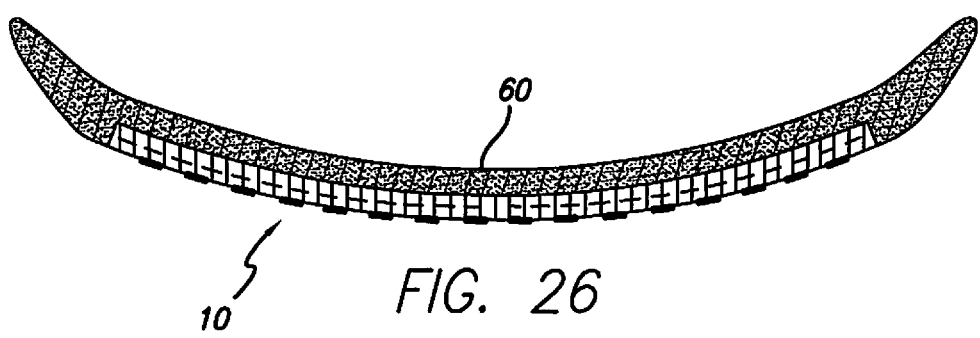
FIG. 26 depicts a flexible circuit array with a protective skirt bonded to the back side of the flexible circuit array and molded around the edges of the flexible circuit array and flush with the front side of the array with a progressively decreasing radius.
Figure 27A:
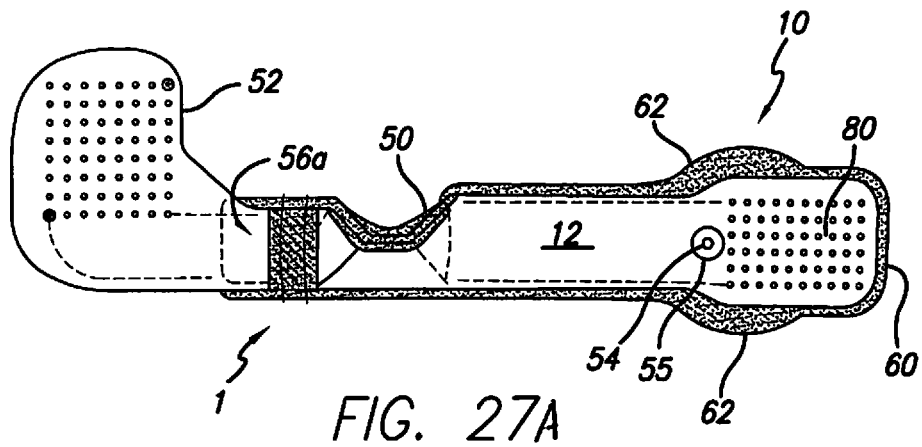
FIG. 27A depicts a side view of the flexible circuit array with a skirt containing a grooved and rippled pad instead of a suture tab.
Figure 27B:
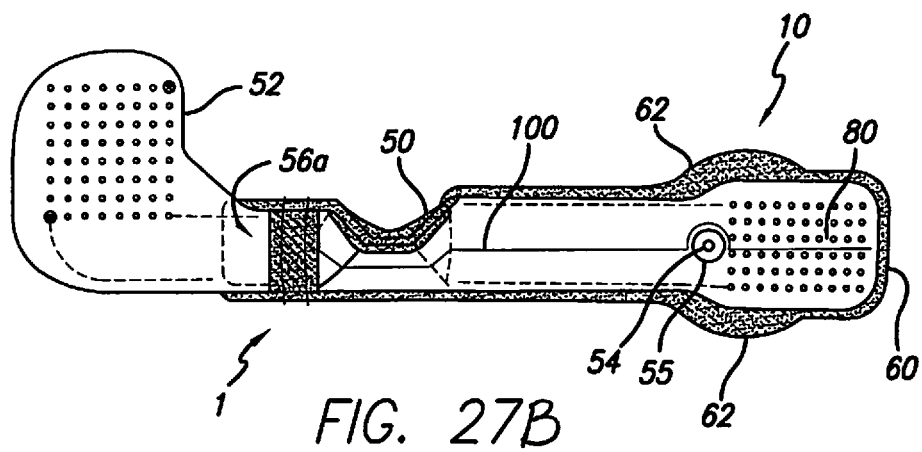
FIG. 27B depicts a side view of the flexible circuit array with a skirt containing a grooved and rippled pad instead of a suture tab with a wire.
Figure 27C:
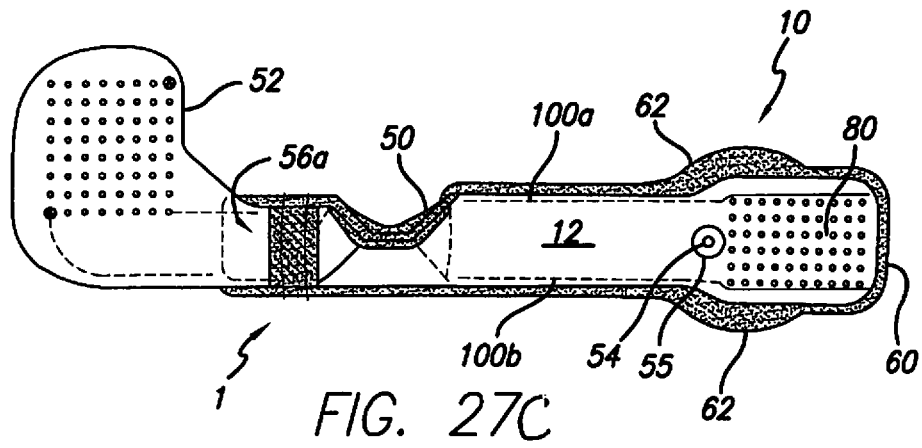
FIG. 27C depicts a side view of the flexible circuit array with a skirt containing a grooved and rippled pad instead of a suture tab with two wires.
Figure 27D:
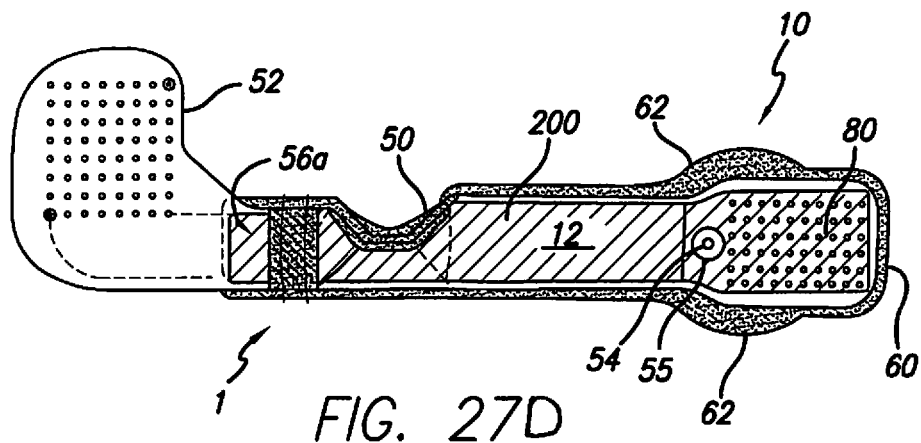
FIG. 27D depicts a side view of the flexible circuit array with a skirt containing a grooved and rippled pad instead of a suture tab with a film or foil.
Figure 28A:
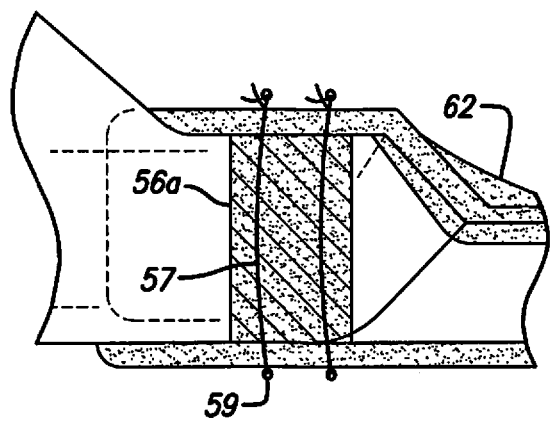
FIG. 28A depicts a side view of the enlarged portion of the skirt shown in FIG. 27A containing a grooved and rippled pad and a mattress suture.
Figure 28B:
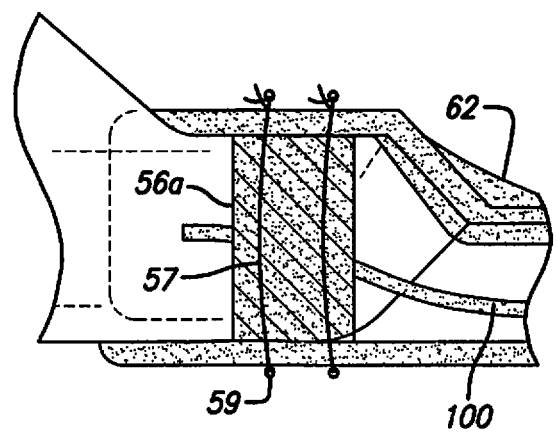
FIG. 28B depicts a side view of the enlarged portion of the skirt shown in FIG. 27B containing a grooved and rippled pad and a mattress suture with a wire.
Figure 28C:
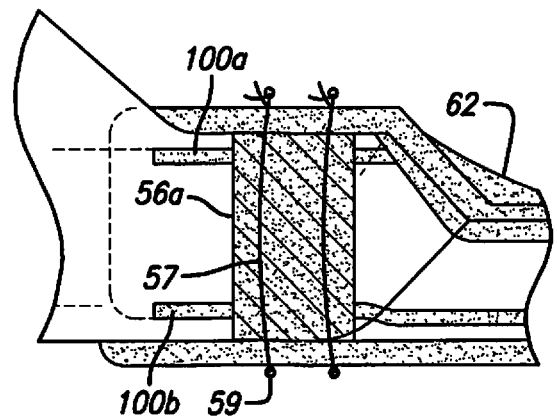
FIG. 28C depicts a side view of the enlarged portion of the skirt shown in FIG. 27C containing a grooved and rippled pad and a mattress suture with two wires.
Figure 28D:
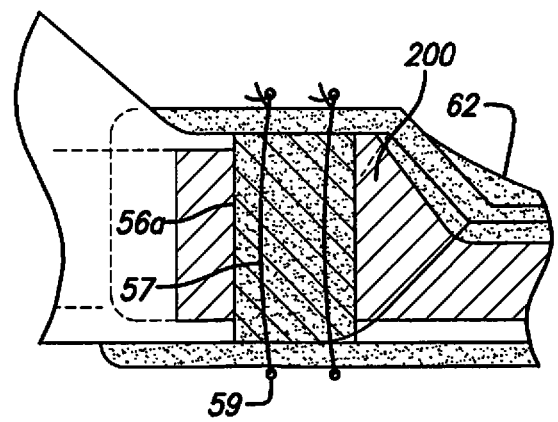
FIG. 28D depicts a side view of the enlarged portion of the skirt shown in FIG. 27D containing a grooved and rippled pad and a mattress suture with a film or foil.

FIG. 26 depicts a flexible circuit array 10 with a protective skirt 60 bonded to the back side of the flexible circuit array 10 and molded around the edges of the flexible circuit array and flush with the front side of the array with a progressively decreasing radius.

FIGS. 27A-27D depict a side view of the array with a skirt 60 containing a grooved and rippled pad 56a instead of a suture tab 56. This pad 56a has the advantage of capturing a mattress suture 57. A mattress suture 57 has the advantage of holding the groove or rippled pad 56a in two places as shown in FIGS. 28A-28D. Each suture 57 is fixed on the tissue in two places 59. A mattress suture 57 on a grooved or rippled mattress 56a therefore provides better stability.

Figure 29:
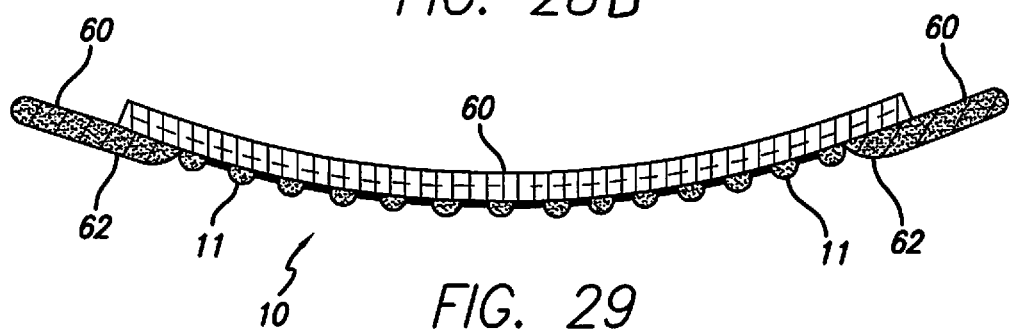
FIG. 29 depicts a flexible circuit array with a protective skirt bonded to the front side of the flexible circuit array with individual electrode windows.

FIG. 29 depicts a flexible circuit array 10 with a protective skirt 60 bonded to the front side of the flexible circuit array 10 with individual electrode 13 windows and with material, preferably silicon between the electrodes 13.

Figure 30:
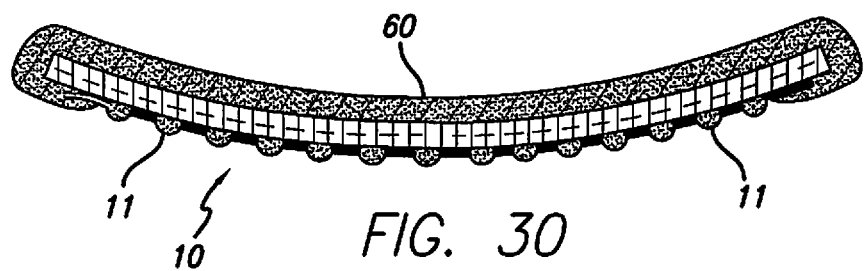
FIG. 30 depicts a flexible circuit array with a protective skirt bonded to the back side of the flexible circuit array and molded around the edges of the flexible circuit array with individual electrode windows.
Figure 37A:
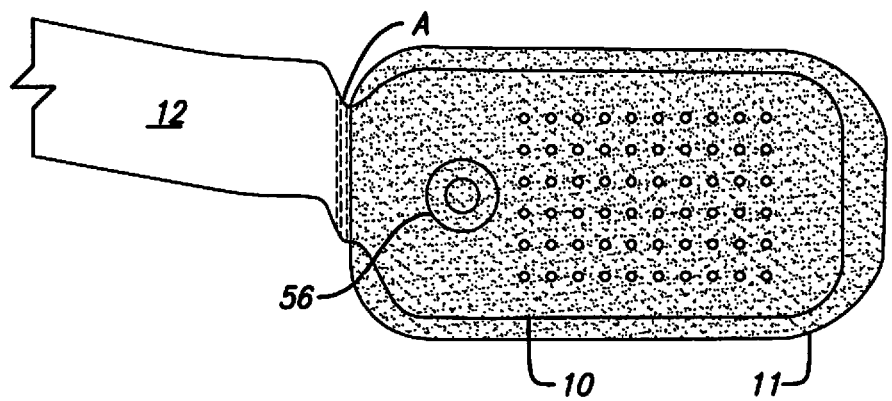
FIG. 37A depicts the top view of the flexible circuit array being enveloped within an insulating material.
Figure 37B:
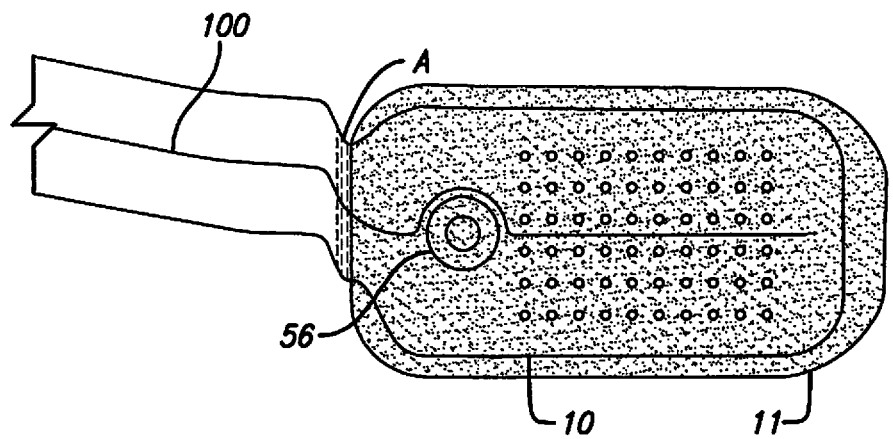
FIG. 37B depicts the top view of the flexible circuit array being enveloped within an insulating material with a wire.
Figure 37C:
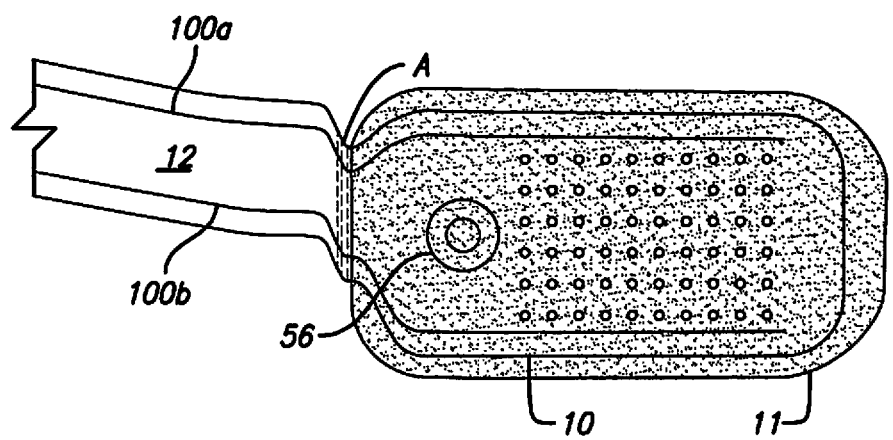
FIG. 37C depicts the top view of the flexible circuit array being enveloped within an insulating material with two wires.
Figure 37D:
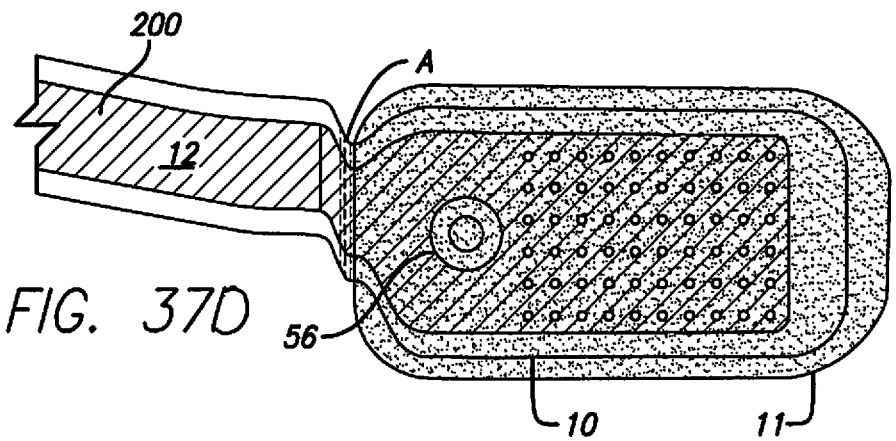
FIG. 37D depicts the top view of the flexible circuit array being enveloped within an insulating material with a film or foil.

FIG. 30 depicts a flexible circuit array with a protective skirt bonded to the back side of the flexible circuit array and molded around the edges of the flexible circuit array with individual electrode windows and with material, preferably silicon, between the electrodes 13.

FIGS. 31-36 show several surfaces to be applied on top of the cable. The surfaces are thin films containing a soft polymer, preferably silicone. FIG. 31 shows a flange 15: A flange 15 can be a solid film of material containing silicone added to the surface of the polymer containing polyimide. FIGS. 32-34 show a ladder 15a: A ladder 15a is a flange with material removed from central portions in some shape 19. FIG. 35 shows a skeleton structure 15b. A skeleton 15b is a flange with material removed from perimeter portions in some shape 21. FIG. 36 shows a structure 15c with beads 23 and bumpers 25. A bead 23 is material added to perimeter portions of the polymer cable in some shape without material being added on the central area. A bumper 25 can be an extended or continuous version of the beaded approach. Both approaches are helpful in preventing any possible injury of the tissue by the polymer.

FIGS. 37A-37D depict the top view of the flexible circuit array 10 being enveloped within an insulating material 11. The electrode array 10 comprises oval-shaped electrode array body 10, a plurality of electrodes 13 made of a conductive material, such as platinum or one of its alloys, but that can be made of any conductive biocompatible material such as iridium, iridium oxide or titanium nitride. The electrode array 10 is enveloped within an insulating material 11 that is preferably silicone. "Oval-shaped" electrode array body means that the body may approximate either a square or a rectangle shape, but where the corners are rounded. This shape of an electrode array is described in the U.S. Patent Application No. 2002/0111658, entitled "Implantable retinal electrode array configuration for minimal retinal damage and method of reducing retinal stress" and No. 2002/0188282, entitled "Implantable drug delivery device" to Rober J. Greenberg et al.; the disclosures of both are incorporated herein by reference.

The material body 11 is made of a soft material that is compatible with the electrode array body 10. In a preferred embodiment the body 11 made of silicone having a hardness of about 50 or less on the Shore A scale as measured with a durometer. In an alternate embodiment the hardness is about 25 or less on the Shore A scale as measured with a durometer.

Figure 38:
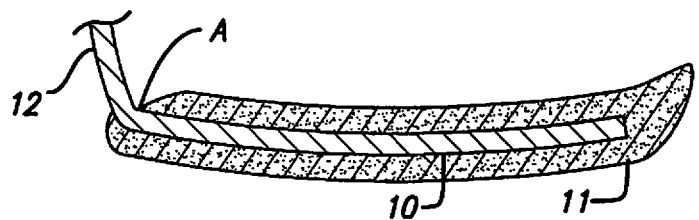
FIG. 38 depicts a cross-sectional view of the flexible circuit array being enveloped within an insulating material.

FIG. 38 depicts a cross-sectional view of the flexible circuit array 10 being enveloped within an insulating material 11. It shows how the edges of the material body 11 are lifting off due to the contracted radius. The electrode array 10 preferably also contains a fold A between the cable 12 and the electrode array 10. The angle of the fold A secures a relief of the implanted material.

Figure 39:
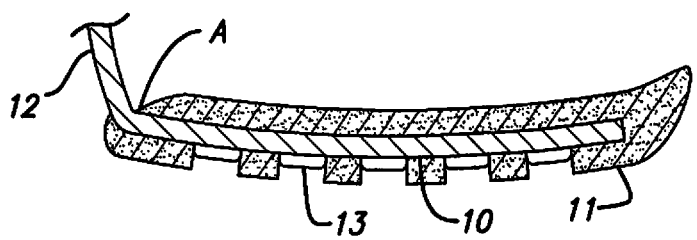
FIG. 39 depicts a cross-sectional view of the flexible circuit array being enveloped within an insulating material with open electrodes and the material between the electrodes.

FIG. 39 depicts a cross-sectional view of the flexible circuit array 10 being enveloped within an insulating material 11 with open electrodes 13 and the material 11 between the electrodes 13. This embodiment also has relief between the body 10 and the retina.

Figure 40:
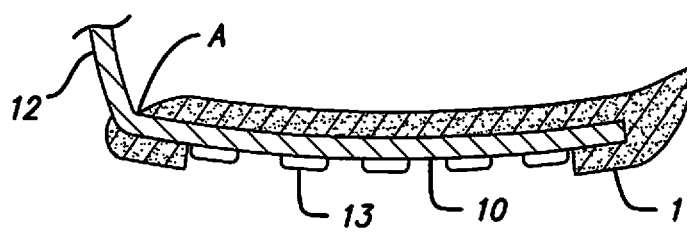
FIG. 40 depicts a cross-sectional view of the flexible circuit array being enveloped within an insulating material with open electrodes.

FIG. 40 depicts a cross-sectional view of the flexible circuit array 10 being enveloped within an insulating material 11 with open electrodes 13. This is another embodiment wherein the electrodes 13 are not separated by the material 11 but the material 11 is extended so that the electrodes 13 are prevented from direct contact with the retina.

Figure 41:
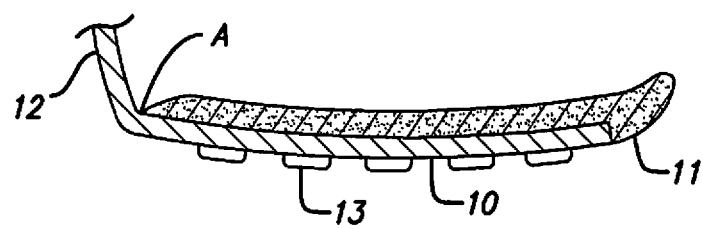
FIG. 41 depicts a cross-sectional view of the flexible circuit array being enveloped within an insulating material with electrodes on the surface of the material.

FIG. 41 depicts a cross-sectional view of the flexible circuit array 10 being enveloped within an insulating material 11 with electrodes 13 on the surface of the material 11. This is a further embodiment with the electrode 13 on the surface of the material 11, preferably silicone. The embodiments shown in FIGS. 39, 40, and 41 show a preferred body 11 containing silicone with the edges being lifted off from the retina due to the contracted radius of the silicon body 11.

Figure 42:
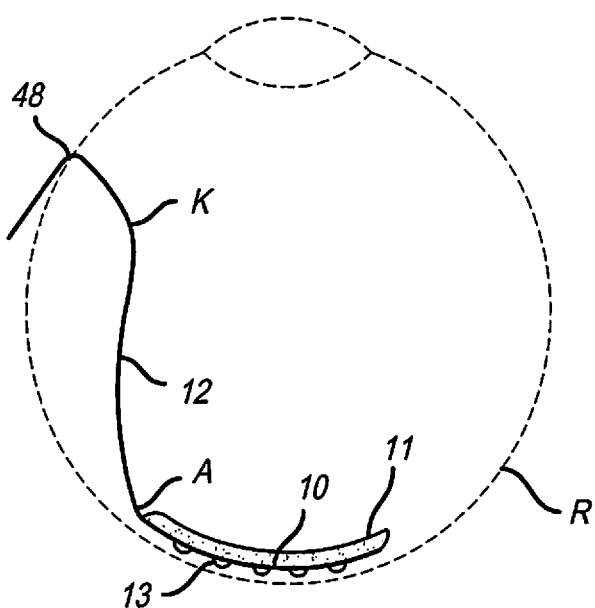
FIG. 42 depicts a cross-sectional view of the flexible circuit array being enveloped within an insulating material with electrodes on the surface of the material inside the eye with an angle in the fold of the flexible circuit cable and a fold between the circuit electrode array and the flexible circuit cable.

FIG. 42 depicts a cross-sectional view of the flexible circuit array 10 being enveloped within an insulating material 11 with electrodes 13 on the surface of the material 11 inside the eye with an angle K in the fold of the flexible circuit cable 12 and a fold A between the circuit electrode array 10 and the flexible circuit cable 12. The material 11 and electrode array body 10 are in intimate contact with the retina R. The surface of the electrode array body 10 in contact with the retina R is a curved surface with a contracted radius compared to the spherical curvature of retina R to minimize stress concentrations therein. Further, the decreasing radius of spherical curvature of material 11 near its edge forms edge relief that causes the edges of the body 11 to lift off the surface of retina R eliminating stress concentrations. The edges of body 11 are strongly lifted off due to the contracted radius of the body 11. The edge of body 11 has a rounded edge eliminating stress and cutting of retina R.

Figure 43:
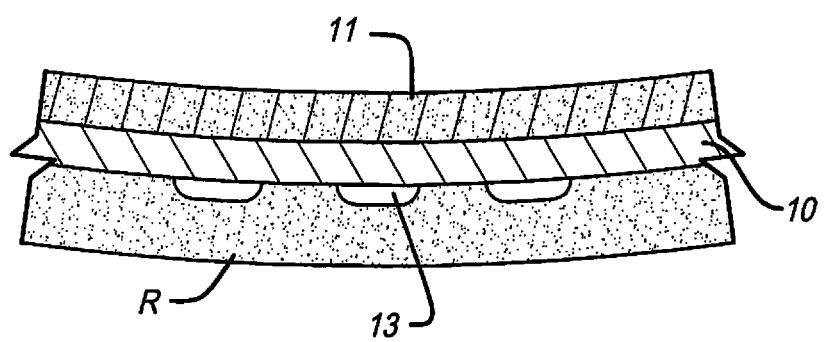
FIG. 43 depicts a side view of the enlarged portion of the flexible circuit array being enveloped within an insulating material with electrodes on the surface of the material inside the eye.

FIG. 43 shows a part of FIG. 42 enlarged, showing the electrode array 10 and the electrodes 13 enveloped by the polymer material, preferably silicone 11, being attached to the retina R.

The electrode array 10 embedded in or enveloped by the polymer material, preferably silicone 11, can be preferably produced through the following steps. The soft polymer material which contains silicone is molded into the designed shape and partially hardened. The electrode array 10 which preferably contains polyimide is introduced and positioned in the partially hardened soft polymer containing silicone. Finally, the soft polymer 11 containing silicone is fully hardened in the designed shape enveloping the electrode array 10. The polymer body 11 has a shape with a contracted radius compared with the retina R so that the edges of the body 11 lift off from the retina R.

The substrate in that process can be silicon or glass. The polymer can be polyimide, thermoplastic polyimide, silicone, Parylene, LCP polymers (Imidex), epoxy resin, urethane, silicone urethane copolymer, or PEEK (Victrex). The metals can be titanium, platinum, palladium, iridium, gold, silver, niobium, titanium nitride, iridium oxide, nickel titanium alloy or other biocompatible metals, or metal alloys or metal layers.

This process could be easily adapted to a multi-metal layer electrode array or similar metal and polymer structures that need to have metal contacts or openings on both sides of the structure.

The traces (metal) are in more than one layer, preferably two or three layers. This variation allows a less broad conductive part of the electrode array. The advantage is that the conductive density is increased. The conductive part can be made thinner by slightly increase of the depth. The increase of depth has only minor influence on the flexibility of the conductive part. The current enters the electrode through a via in the center and not at the edge. If the current is led to the electrode at the edge and the electrode starts to dissolve at the edge to the insulating material it leads to a faster break up of the conductivity. The advantage of the present multilayer is that the conductivity stays stable, because even if the electrode starts to dissolve at the edge of the insulating material, the conductivity stays stable until the electrode dissolves completely towards the center.

The implanted portion of the retinal prosthesis has a gentle twist or fold 48 in the flexible circuit cable 12, where the flexible circuit cable 12 passes through the sclera (sclerotomy) as shown in FIG. 42. The twist may be a simple sharp twist, or fold 48, or it may be a longer twist, forming a tube. While the tube is rounder, it reduces the flexibility of the flexible circuit. A simple fold 48 reduces the width of the flexible circuit with only minimal impact on flexibility. It is important to ensure that the flexible circuit cable 12 stays in shape after the fold is performed.

It has been found, surprisingly, that a support like a wire 100 (see FIGS. 8B, 9B, 10B, 16B, 17B, 18B, 20B, 21B, 22B, 27B, 28B, and 37B) or two wires 100a and 100b (see FIGS. 8C, 9C, 10C, 16C, 17C, 18C, 20C, 21C, 22C, 27C, 28C, and 37C) or a film or foil 200 (see FIGS. 8D, 9D, 10D, 16D, 17D, 18D, 20D, 21D, 22D, 27D, 28D, and 37D) ensures that such a fold or twist, once performed, holds the shape. Such a wire can be one or more electrode traces or even all of the traces. The metal wire or film or foil preferably contain platinum, palladium, gold, silver, titanium, and other biocompatible metals mixture, and alloys thereof. The metal support is embedded length wise in the flexible circuit cable.

The flexible circuit electrode array comprises: a polymer base layer; metal traces deposited on said polymer base layer, including electrodes suitable to stimulate neural tissue; a polymer top layer deposited on said polymer base layer and said metal traces; and a support embedded in said array.

The flexible circuit electrode array is preferred wherein said support is one thin rod, wire, tube, or strip, or said support contains two or more thin rods, wires, tubes, or strips, or said support is film or foil.

The flexible circuit electrode array is preferred wherein said support contains at least one metal, metal alloy, metal layer structure or mixtures thereof and said metal can be titanium, platinum, palladium, iridium, gold, silver, niobium, titanium nitride, iridium oxide, or other biocompatible metal, or metal alloys, or metal layers.

The flexible circuit electrode array is preferred wherein said support contains at least one polymer, copolymer, block copolymer, or mixtures thereof and said polymer is polyimide, thermoplastic polyimide, silicone, Parylene, LCP polymers (Imidex), epoxy resin, or PEEK (Victrex).

The flexible circuit electrode array is preferred wherein said support is embedded at least in the base layer, or said support is embedded at least in the top polymer, or said support is embedded at least between the base and the top polymer.

The flexible circuit electrode array is preferred wherein said support is embedded approximately through the length of the flexible circuit cable portion of said flexible circuit electrode array.

The flexible circuit electrode array is preferred wherein said support has a thickness of 0.1 μm-2 mm, preferably of 1 μm-5 μm.

Figure 47:
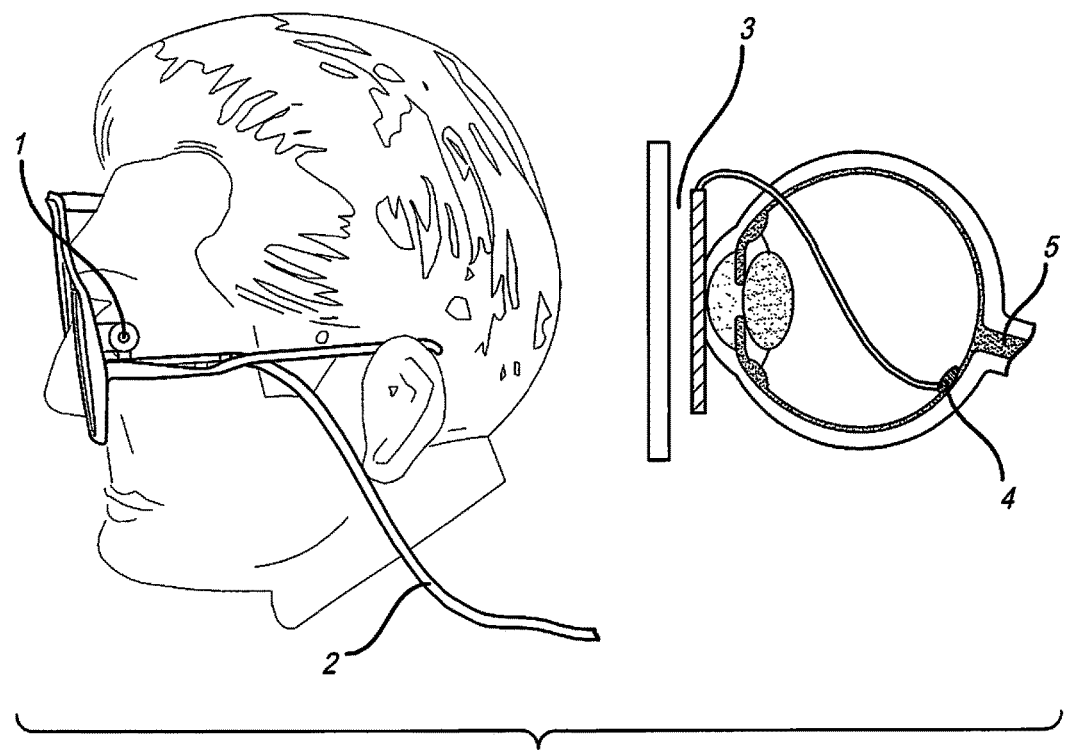
FIG. 47 shows a cross-sectional view of an implanted flexible circuit electrode array with a folded flexible array cable and other parts of the retinal prosthesis.

FIG. 47 shows a cross-sectional view of an implanted flexible circuit electrode array with a folded flexible array cable and other parts of the retinal prosthesis. FIG. 47 shows:
  (1) Camera on glasses which views images
  (2) Signals which are sent to a hand held device
  (3) Processed information is sent back to glasses and wirelessly transmitted to receiver under surface of eye
  (4) Receiver which sends information to electrode in retinal implant
  (5) Electrodes which stimulate retina to send information to the brain.

Figure 48:
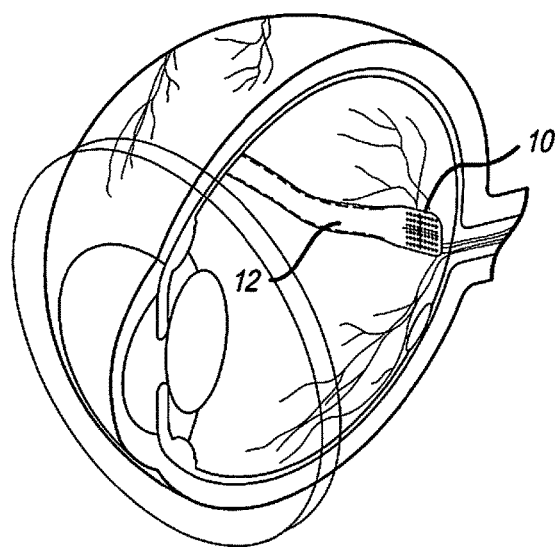
FIG. 48 shows a cross-sectional view of a human eye and implanted flexible circuit electrode array with a folded flexible array cable.

FIG. 48 shows a cross-sectional view of a human eye and implanted flexible circuit electrode array with a folded flexible array cable. The folded cable has advantages as being more stable by having a slight stiffness. The cable can have one fold or more than one fold.

The flexible circuit electrode array comprises: a polymer base layer; metal traces deposited on said polymer base layer, including electrodes suitable to stimulate neural tissue; a polymer top layer deposited on said polymer base layer and said metal traces; and a folded flexible circuit cable connecting the electrode array with an interconnection pad.

The flexible circuit electrode array is preferred wherein said flexible circuit cable has at least one fold.

The flexible circuit electrode array is preferred wherein said flexible circuit cable has at least three folds.

The method of making a flexible circuit electrode array comprises:
depositing a polymer base layer;
depositing metal on said polymer base layer;
patterning said metal to form metal traces;
depositing a polymer top layer on said polymer base layer and said metal traces;
heating said flexible circuit electrode array in a mold to form a three dimensional shape in said flexible circuit electrode array;
embedding a support at least in the base layer, top layer or between the base and top layer; and/or
folding a flexible circuit cable at least once connecting the electrode array with an interconnection pad the array.

Figure 49:
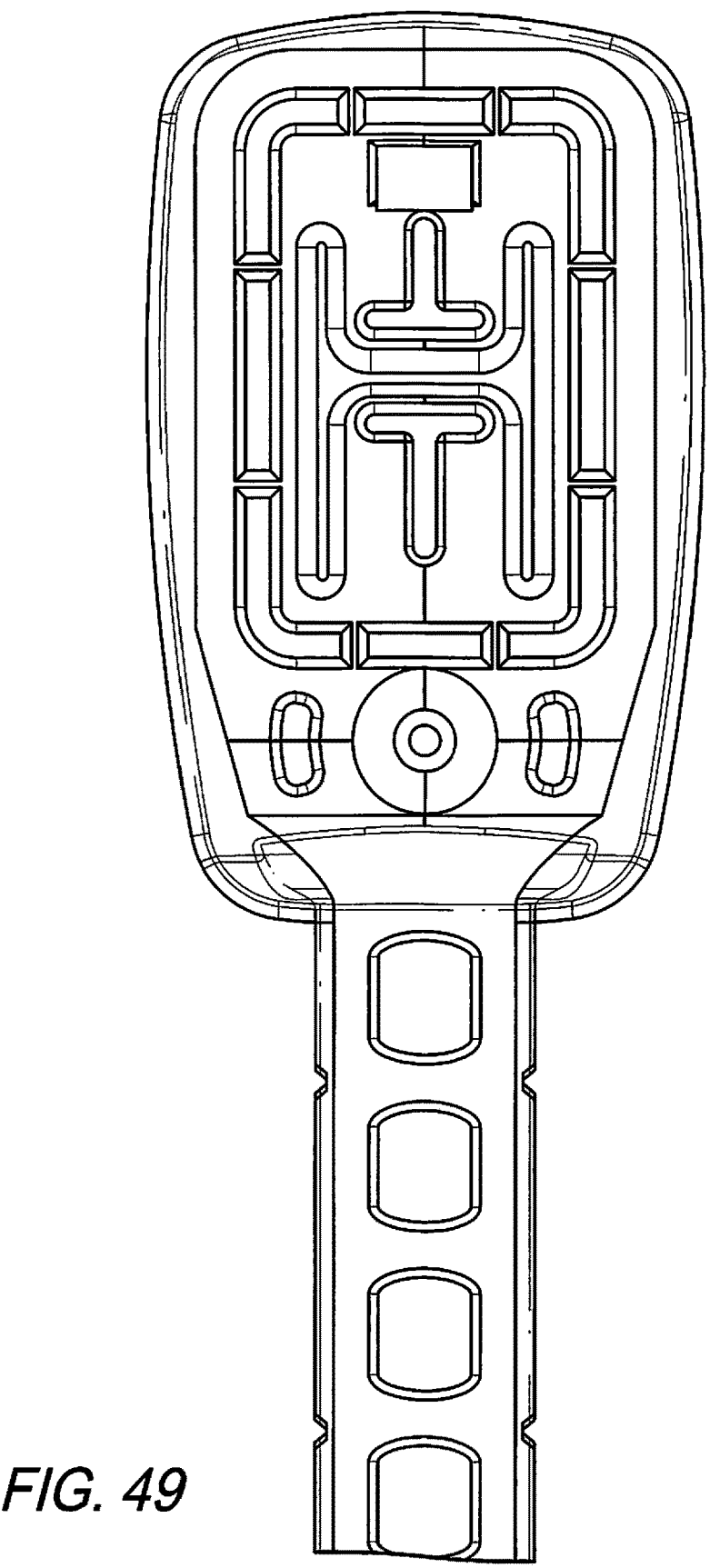
FIG. 49 depicts an alternate view of an over molded flexible circuit array with a polymer support in the shape of H.

FIG. 49 depicts an alternate view of an over molded flexible circuit array with a polymer support in the shape of H.

Figure 44:
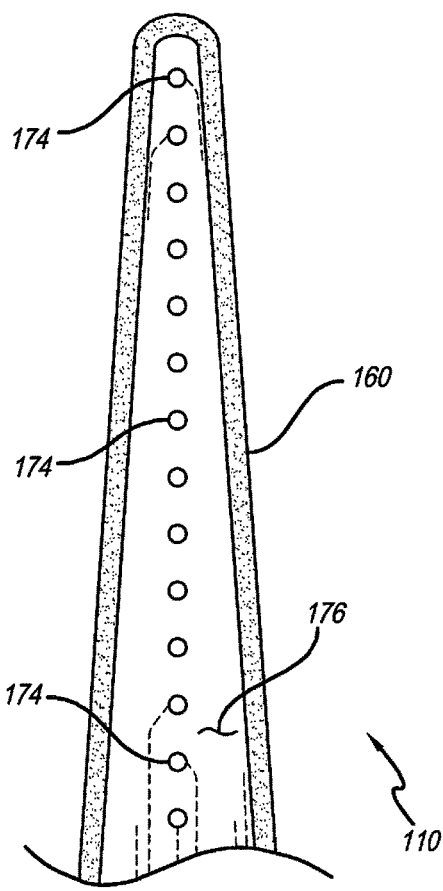
FIG. 44 shows a front view of a cochlear electrode array according to the present invention.
Figure 45:
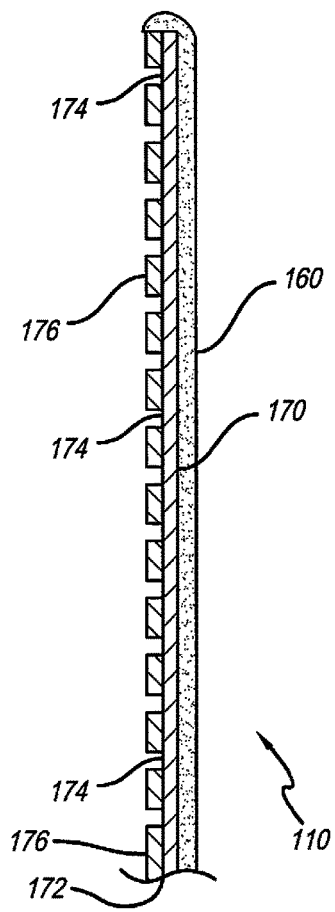
FIG. 45 shows a side view of a cochlear electrode array according to the present invention.
Figure 46:
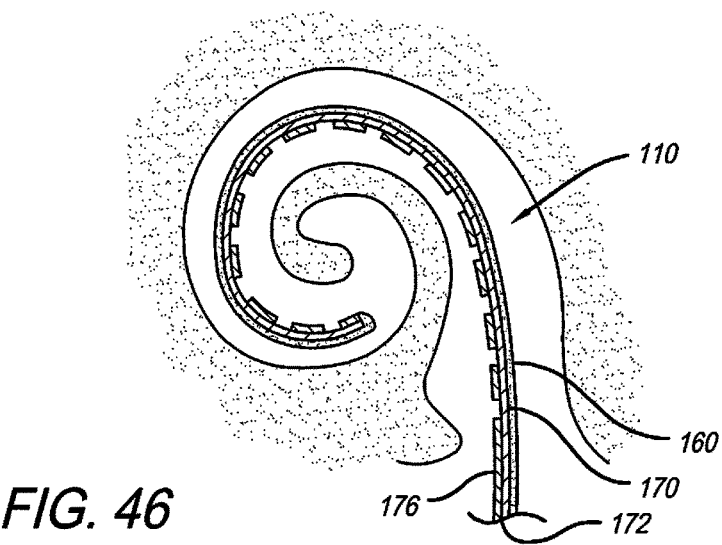
FIG. 46 shows a cochlear electrode array according to the present invention as implanted in the cochlea.

FIGS. 44-46 show application of the present invention to a cochlear prosthesis. FIG. 44 shows the front view of a cochlear electrode array 110. The cochlear electrode array 110 tapers toward the top to fit in an ever smaller cochlea and because less width is required toward the top for metal traces. The electrodes 174 are arranged linearly along the length of the array 110. Further, a skirt 160 of more compliant polymer, such as silicone, surrounds the array 110. FIG. 45 is a side view of the cochlear electrode array 110. The cochlear electrode array 110 includes a bottom polymer layer 170, metal traces 172, and a top polymer layer 176. Openings in the top polymer layer 176 define electrodes 174.

The cochlear electrode array 110 is made flat as shown in FIGS. 44 and 13B. It is then thermoformed, as described above, into a spiral shape to approximate the shape of the cochlea, as shown in FIG. 46. The cochlear electrode array 110 is implanted with the bottom layer 170 formed toward the outside of the curvature, and the top polymer layer 176 toward the inside of the curvature. This is opposite of the thermoforming process used for a retinal array. A cortical array would be thermoformed to curve inward like a cochlear array.

A flexible circuit electrode array comprises: a polymer base layer; metal traces deposited on said polymer base layer, including electrodes suitable to stimulate neural tissue; a polymer top layer deposited on said polymer base layer and said metal traces; and a support embedded in said array.

The flexible circuit electrode array is preferred, wherein said polymer base layer, said metal traces, and said polymer top layer are curved to approximately the curvature of an eye.

The flexible circuit electrode array is preferred, wherein said polymer base layer, said metal traces, and said polymer top layer are thermoformed in a three dimensional shape.

The flexible circuit electrode array is preferred, which further comprises at least one bumper bonded to a peripheral edge of said flexible circuit electrode array.

The flexible circuit electrode array is preferred, wherein said polymer top layer is a more compliant polymer than said polymer base layer.

The flexible circuit electrode array is preferred, which further comprises a stress relief membrane suitable for attachment of said flexible circuit electrode array, wherein said stress relief membrane is a more compliant material than said polymer base layer.

The flexible circuit electrode array is preferred, which further comprises a narrowed portion in a flexible circuit cable portion of said flexible circuit electrode array.

The flexible circuit electrode array is preferred, wherein said narrowed portion is suitable to pierce a sclera.

The flexible circuit electrode array is preferred, which further comprises diagonal fold in a flexible circuit cable portion of said flexible circuit electrode array.

The flexible circuit electrode array is preferred, where said diagonal fold is across a dogleg in said flexible circuit electrode array.

The flexible circuit electrode array is preferred, which further comprises bond pads coupled to said metal traces on an end of said flexible circuit electrode array opposite to said electrodes and openings in said polymer top layer for said electrodes and said bond pads.

The flexible circuit electrode array is preferred, wherein said fold forms a narrowed portion.

The flexible circuit electrode array is preferred, which further comprises a widened portion of a flexible circuit cable portion of said flexible circuit electrode array suitable to resist movement of said flexible circuit electrode array.

The flexible circuit electrode array is preferred, wherein said flexible circuit electrode array is suitable to be implanted in an eye and said widened portion is suitable to resist movement of said flexible circuit electrode array through a sclera.

The flexible circuit electrode array is preferred, which further comprises a bumper bonded to a peripheral edge of said flexible circuit electrode array.

The flexible circuit electrode array is preferred, which further comprises at least one bumper bonded to a flexible circuit cable portion of said flexible circuit electrode array.

The flexible circuit electrode array is preferred, where said bumper is a continuous skirt covering at least a portion of said flexible circuit electrode array.

The flexible circuit electrode array is preferred, wherein said bumper is a continuous skirt covering at least a portion of a cable portion of said flexible circuit electrode array.

The flexible circuit electrode array is preferred, which further comprises a sleeve at least partially covering a flexible circuit cable portion of said flexible circuit electrode array.

The flexible circuit electrode array is preferred, wherein said sleeve and said bumper are a continuous body.

The flexible circuit electrode array is preferred, wherein said polymer base layer, said metal traces and said polymer top layer form a continuous electrode array and flexible circuit cable where said flexible circuit cable forms a partial loop to resist transmission of forces through said flexible circuit cable.

The flexible circuit electrode array is preferred, wherein said polymer top layer defines openings smaller than said electrodes to overlap said electrodes.

The flexible circuit electrode array is preferred, wherein a polymer top layer is deposited on said polymer base layer and said metal traces; and wherein said polymer base layer, said metal traces and said polymer top layer are thermoformed in a three dimensional shape.

The flexible circuit electrode array is preferred, wherein the flexible circuit cable portion has a fold with the attached flexible circuit electrode array with an angle of about 1° to about 180°.

The flexible circuit electrode array is preferred, wherein the flexible circuit cable portion comprises at least one grooved or rippled pad for capturing a mattress suture.

The flexible circuit electrode array is preferred, which further comprises a slit along the length axis of said flexible circuit electrode array.

The flexible circuit electrode array is preferred, which further comprises a slit along the length axis of said flexible circuit electrode array and a central attachment point.

The flexible circuit electrode array is preferred, which further comprises a slit along the length axis of said flexible circuit electrode array and two attachment points located outside of the flexible circuit electrode array and positioned apart as far as possible from each other.

The flexible circuit electrode array is preferred, wherein the flexible circuit electrode array has a contracted radius compared to the radius of the hosting eye.

The flexible circuit electrode array is preferred, wherein the flexible circuit electrode array contains soft insulating material on the surface between the electrodes.

The flexible circuit electrode array is preferred, wherein the material contains silicone.

The flexible circuit electrode array is preferred, wherein a film containing a soft polymer is applied on the flexible circuit cable portion.

The flexible circuit electrode array is preferred, wherein a film containing a soft polymer contains silicone.

The flexible circuit electrode array is preferred, wherein a film containing a soft polymer comprises a structure like a ladder, or flange skeleton.

The flexible circuit electrode array is preferred, wherein a film containing a soft polymer contains beads and/or bumpers.

A flexible circuit electrode array further comprises: a polymer base layer; metal traces deposited on said polymer base layer, including electrodes suitable to stimulate neural tissue; and said polymer base layer and said metal traces are embedded in a body having a generally oval shape in the plane of the retina, said oval shaped body being curved such that it substantially conforms to the spherical curvature of the retina of the recipient's eye.

The flexible circuit electrode array is preferred, comprising at least one mounting aperture in said body for attaching the electrode array to the retina with a tack.

The flexible circuit electrode array is preferred, wherein said oval shaped body has a radius of spherical curvature, which is smaller than the radius of the curvature of the eye.

The flexible circuit electrode array is preferred, wherein said oval shaped body is made of a soft polymer containing silicone having hardness of about 70 or less on the Shore A scale as measured with a durometer.

The flexible circuit electrode array is preferred, wherein said flexible circuit cable portion comprises at least one grooved or rippled pad for capturing a mattress suture.

The flexible circuit electrode array is preferred, wherein said flexible circuit electrode array is positioned on the surface of the body having a generally oval shape.

The flexible circuit electrode array is preferred, wherein soft insulating material is positioned on the surface between said electrodes.

The flexible circuit electrode array is preferred, wherein a film containing a soft polymer is applied onto said flexible circuit cable portion.

The flexible circuit electrode array is preferred, wherein said film containing a soft polymer contains silicone.

The flexible circuit electrode array is preferred, wherein said film containing a soft polymer comprises a ladder like structure.

The flexible circuit electrode array is preferred, wherein a film containing a soft polymer contains beads and/or bumpers.

A method of making a flexible circuit electrode array comprises: depositing a polymer base layer; depositing metal on said polymer base layer; patterning said metal to form metal traces; depositing a polymer top layer on said polymer base layer and said metal traces; and heating said flexible circuit electrode array in a mold to form a three dimensional shape in said flexible circuit electrode array.

The method is preferred, which further comprises the steps of heating said flexible circuit electrode array in successively smaller molds.

The method is preferred, wherein said step of depositing said polymer base layer and said polymer top layer is depositing polyimide.

The method is preferred, wherein said step of depositing said polymer base layer and said polymer top layer is depositing silicone.

The method is preferred, wherein said step of depositing said polymer base layer and said polymer top layer is depositing fluoro-polymer.

The method is preferred, which further comprises forming a twist in a flexible circuit cable portion of said flexible circuit electrode array.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

The invention claimed is:

1. A flexible circuit electrode array comprising:
a polymer base layer;
a metal trace layer deposited on the polymer base layer, the metal trace layer including a two dimensional array of electrodes configured to stimulate neural tissue defining an electrode field within an electrode array portion, a two dimensional array of bond pads configured to attach to an electronic circuit package defining a bond pad portion and traces defining a cable portion between the electrode array portion and the bond pad portion connecting the electrodes to the bond pads, the metal trace layer being thicker at the electrodes and bond pads;
a polymer top layer deposited on the polymer base layer and deposited on the metal trace layer; and
at least one support embedded in the flexible circuit electrode array, outside the electrode field, not electrically connected to the electrodes or the bond pads, in addition to the metal trace layer, wherein the at least one embedded support is of a material suitable to be manually bent when implanted ensuring better shape control and pressure uniformity, and that a fold or twist once manually made upon implantation holds its shape better than without the at least one embedded support.

2. The flexible circuit electrode array according to claim 1, wherein the embedded support comprises at least one wire, film, foil, rod, tube, or strip embedded in the cable.

3. The flexible circuit electrode array according to claim 1, where the support is embedded lengthwise through the cable portion.

4. The flexible circuit electrode array according to claim 1, wherein the at least one embedded support is comprised of two or more thin rods, wires, tubes or strips.

5. The flexible circuit electrode array according to claim 1, wherein the at least one embedded support is comprised of film or foil.

6. The flexible circuit electrode array according to claim 1, wherein the at least one embedded support comprises at least one metal, metal alloy, metal layer structure, or mixtures thereof.

7. The flexible circuit electrode array according to claim 1, wherein the embedded support is comprised of titanium, platinum, palladium, iridium, gold, silver, niobium, titanium nitride, iridium oxide, other biocompatible metal, metal alloys, or metal layers.

8. The flexible circuit electrode array according to claim 1, wherein the at least one embedded support comprises at least one polymer, copolymer, block copolymer or mixtures thereof.

9. The flexible circuit electrode array according to claim 8, wherein the polymer base layer comprises polyimide, thermoplastic polyimide, Parylene, liquid crystal polymers (LCP), epoxy resin, polyaryletherketones (PEEK), or a fluoropolymer.

10. The flexible circuit electrode array according to claim 1, wherein the at least one support embedded in the flexible circuit electrode array is embedded at least in the polymer base layer.

11. The flexible circuit electrode array according to claim 1, wherein the at least one support embedded in the flexible circuit electrode array is embedded at least in the polymer top layer.

12. The flexible circuit electrode array according to claim 1, wherein the at least one support embedded in the flexible circuit electrode array is embedded at least between the polymer base layer and the polymer top layer.

13. The flexible circuit electrode array according to claim 1, wherein the at least one embedded support has a thickness of 0.1 micrometer to 2 mm.

14. The flexible circuit electrode array according to claim 1, wherein the at least one embedded support has a thickness of 1 micrometer to 5 micrometers.

15. The flexible circuit electrode array according to claim 1, wherein the at least one embedded support comprises notches, spikes, or a coil to improve adhesion between the support and the polymer base layer or the polymer top layer.

* * * * *